(12) United States Patent
Nicolaisen et al.

(10) Patent No.: US 11,573,229 B2
(45) Date of Patent: Feb. 7, 2023

(54) ISOLATION OF FETAL CELLS USING FACS

(71) Applicant: Arcedi Biotech ApS, Vejle (DK)

(72) Inventors: Bolette Hestbek Nicolaisen, Vejle (DK); David Mathias Martin Leiding Kolvraa, Vejle (DK); Inga Baasch Christensen, Vejle (DK); Katarina Ravn, Veijle (DK); Line Dahl Jeppesen, Vejle (DK); Lotte Hatt, Vejle (DK); Palle Scheide Jensen, Vejle (DK); Ripudaman Singh, Vejle (DK)

(73) Assignee: Arcedi Biotech ApS, Vejle (DK)

(*) Notice: Subject to any disclaimer, the term of this patent is extended or adjusted under 35 U.S.C. 154(b) by 0 days.

(21) Appl. No.: 17/182,749

(22) Filed: Feb. 23, 2021

(65) Prior Publication Data

US 2021/0199664 A1 Jul. 1, 2021

Related U.S. Application Data

(63) Continuation of application No. PCT/EP2020/065832, filed on Jun. 8, 2020.

(30) Foreign Application Priority Data

Jun. 7, 2019 (EP) .................................... 19179087

(51) Int. Cl.
| | |
|---|---|
| G01N 33/569 | (2006.01) |
| C12N 5/073 | (2010.01) |
| C12Q 1/6883 | (2018.01) |
| G01N 33/543 | (2006.01) |
| G01N 33/68 | (2006.01) |

(52) U.S. Cl.
CPC ..... *G01N 33/56966* (2013.01); *C12N 5/0603* (2013.01); *C12Q 1/6883* (2013.01); *G01N 33/54326* (2013.01); *G01N 33/689* (2013.01); *C12Q 2600/156* (2013.01); *G01N 2800/368* (2013.01)

(58) Field of Classification Search
CPC ....... G01N 33/56966; G01N 33/54326; C12N 5/0603; C12Q 1/6883; C12Q 2600/15
See application file for complete search history.

(56) References Cited

U.S. PATENT DOCUMENTS

| | | |
|---|---|---|
| 5,648,222 A | 7/1997 | Tse et al. |
| 5,714,325 A | 2/1998 | Bianchi |
| 5,861,253 A | 1/1999 | Asgari et al. |
| 2003/0036100 A1 | 2/2003 | Fisk et al. |
| 2003/0148295 A1 | 8/2003 | Wan et al. |
| 2004/0096392 A1 | 5/2004 | Bhaskar et al. |
| 2005/0003351 A1 | 1/2005 | Fejgin et al. |
| 2005/0049793 A1 | 3/2005 | Paterlini-Brechot |
| 2007/0015171 A1 | 1/2007 | Bianchi |
| 2008/0261822 A1 | 10/2008 | Fejgin et al. |

FOREIGN PATENT DOCUMENTS

| | | | |
|---|---|---|---|
| EP | 1302533 A1 | 4/2003 | |
| EP | 2638176 A1 | 9/2013 | |
| EP | 2638176 B1 * | 8/2017 | ....... G01N 33/56966 |
| WO | 1994/022646 A1 | 10/1994 | |
| WO | 1995/03431 | 2/1995 | |
| WO | 1997/30354 A1 | 8/1997 | |
| WO | 2001/79851 A1 | 10/2001 | |
| WO | 2006/097051 A1 | 9/2006 | |
| WO | 2006/119569 A1 | 11/2006 | |
| WO | 2007/065438 A2 | 6/2007 | |
| WO | 2007/065438 A3 | 7/2007 | |
| WO | 2008/017871 A1 | 2/2008 | |
| WO | 2008/132753 A2 | 11/2008 | |
| WO | 2009/103110 A1 | 8/2009 | |
| WO | 2010/078872 A2 | 7/2010 | |
| WO | 2010/121315 A1 | 10/2010 | |
| WO | 2012/062325 A1 | 5/2012 | |

OTHER PUBLICATIONS

Tse et al. Characterization of trophoblast-reactive monoclonal antibodies by flow cytometry and their application for fetal cell isolation. Ann N Y Acad Sci. Sep. 7, 1994;731:162-9. doi: 10.1111/j.1749-6632.1994.tb55763.x.*
Breman et al. Evidence for feasibility of fetal trophoblastic cell-based noninvasive prenatal testing. Prenat Diagn. Nov. 2016; 36(11):1009-1019. Published online Oct. 2, 2016. doi:10.1002/pd.4924.*
Sabbatinelli et al. Isolation and Enrichment of Circulating Fetal Cells for NIPD: An Overview. Diagnostics (Basel). Nov. 30, 2021;11(12):2239. doi: 10.3390/diagnostics11122239. PMID: 34943476; PMCID: PMC8700692.*
Bianchi et al. Fetal gender and aneuploidy detection using fetal cells in maternal blood: analysis of NIFTY I data. National Institute of Child Health and Development Fetal Cell Isolation Study. Prenat Diagn. Jul. 2002;22(7):609-15. doi: 10.1002/pd.347. PMID: 12124698.*
Hu et al. Single Cell Isolation and Analysis. Front. Cell Dev. Biol. Oct. 25, 2016;4:116. doi: 10.3389/fcell.2016.00116. eCollection 2016.*
Kögler, Gesine et al., A New Human Somatic Stem Cell from Placental Cord Blood with Intrinsic Pluripotent Differentiation Potential, J. Exped. Med; vol. 200, No. 2, Jul. 19, 2004.
Lipovsek et al., In-vitro protein evolution by ribosome display and mRNA display, J. Imm. Methods, 290, pp. 51-67, 2004.
Lopresti et al., Sensitive and easy screening for circulating tumor cells by flow cytometry, JCI Insight, 4(14): e128180, 2019.
Maron et al., Gene expression analysis in pregnant women and their infants identifies unique fetal biomarkers that circulate in maternal blood, J of Clinical Investigation, 117(10): 3007-3019, Oct. 2007.

(Continued)

*Primary Examiner* — Gregory S Emch
(74) *Attorney, Agent, or Firm* — Dinsmore & Shohl LLP; Weston R. Gould

(57) ABSTRACT

The present invention relates to automated methods for isolating fetal cells from a sample, such as a blood sample, derived from a pregnant woman. The isolated fetal cells can be used for identifying genetic abnormalities in the fetal DNA.

19 Claims, 22 Drawing Sheets

(56) References Cited

OTHER PUBLICATIONS

McCafferty et al., Phage antibodies: filamentous phage displaying antibody variable domains, Nature, Dec. 6;348 (6301):552-4, 1990.
Meyer et al., Maternal serum placental alkaline phosphatase level and risk for preterm delivery, Am. J. Obstet. Gynecol; 1995, vol. 173(1); pp. 181-186.
Na, Kyu-Hwan et al., Isolation and Characterization of Trophoblast Stem Cells-like Cells Derived from Human Term Placenta, Dev. Reprod. vol. 14, No. 3, 155-162, 2010.
Neves et al., Genomic High-Resolution Profiling of Single CKpos/CD45neg Flow-Sorting Purified Circulating Tumor Cells from Patients with Metastatic Breast Cancer, Clinical Chemistry 60:10, 1290-1297, 2014.
Odegrip et al., CIS display: In vitro selection of peptides from libraries of protein-DNA complexes, Proc Natl Acad Sci USA, 101(9):2806-10, 2004.
O'Donoghue et al., Identification of fetal mesenchymal stem cells in maternal blood: implications for non-invasive prenatal diagnosis, Molecular Human Reproduction; vol. 9, No. 8; pp. 497-502, 2003.
Pack et al., Miniantibodies: Use of Amphipathic Helices to Produce Functional, Flexibly Linked Dimeric Fv Fragments with High Avidity in *Escherichia coli*, Biochemistry, 31(6):1579-84, 1992.
Parsons et al., Directing phage selections towards specific epitopes, Protein Engineering, Oxford University Press, Surrey, GB, vol. 9, No. 11, 1996, p. 1043-1049.
Purwosuno et al., Clinical Potential for Noninvasive prenatal diagnosis through detection of fetal cells in maternal blood, Taiwanese J Obstet Gynecol, 45(1): 10-20, Mar. 2006.
Quan et al., Identification of genes preferentially expressed in mammary epithelial cells of Copenhagen rat using subtractive hybridization and microarrays, Carcinogenesis, vol. 24 No. 10, pp. 1593-1599, 2003.
Radunovic et al., Fetal and maternal plasma endothelin levels during the second half of pregnancy, Am J Obstetrics and Gynecology, vol. 172(1), 1995; pp. 28-32.
Soncini et al., Isolation and characterization of mesenchymal cells from human fetal membranes, Journ. Tissue Engineering and Regenerative Medicine, vol. 1; 2007; pp. 296-305.
Swennenhuis et al., Efficiency of whole genome amplification of single circulating tumor cells enriched by CellSearch and sorted by FACS, Genome Medicine, 5:106, pp. 1-11, 2013.
Sørensen et al., Microselection—affinity selecting antibodies against a single rare cell in a heterogeneous population, J. Cell. Mol. Med. vol. 14, No. 7, pp. 1953-1961, 2010.
Tanaka et al., In Situ Phage Screening. A method for identification of subnanogram tissue components in situ, Journal of Biology Chemistry, vol. 277, No. 33, Aug. 16, 2002 (Aug. 16, 2002) p. 30382-30387.
Tordsson et al., Efficient selection of scFv antibody phage by absorption to in situ expressed antigens in tissue selections, Journal of Immunological Methods, Elsevier Science Publishers B.V., Amsterdam, NL, 210(1): 11-23, Dec. 12, 1997.
Vallejo et al., Accumulation of Large Conductance Ca2+-Activated K+ (MaxiK) Channels into the Sarcoplasmic Reticulim in Mouse Myometrium during Late Pregnance, Anesthesiology Abstracts, 103; A565, 2005.
Vicovac et al., Epithelial-mesenschymal transition during trophoblast differentiation, Acta Anatomica, vol. 156(3); 1996; pp. 202-216.
Vossaert el al., Validation Studies for Single Circulating Trophoblast Genetic Testing as a Form of Noninvasive Prenatal Diagnosis, The American Journal of Human Genetics, 105: 1-12, Dec. 5, 2019.
Voullaire et al., Fetal nucleated red blood cells from CVS washings: an aid to development of first trimester non-invasice prenatal diagnosis, Prenatal Diagnosis, vol. 21, No. 10, 2001, 827-834.
Wada et al., Method of separation and concentration of fetal nucleated red blood cells in maternal blood and its application to fetal diagnosis, Congenital Anomalies, 44: 72-78, 2004.
Wang et al., Fetal Nucleated Erythrocyte Recovery: Fluorescence Activated Cell Sorting-Based Positive Selection Using Anti-Gamma Globin Versus Magnetic Activated Cell Sorting Using Anti-CD45 Depletion and Anti-Gamma Globin Positive Selection, Cytometry 39:224-230, 2000.
Winter et al., Making antibodies by phage display technology, Annu Rev Immunol., 12:433-55, 1994.
Yao et al., Targeting pancreatic islets with phage display assisted by laser pressure catapult microdissection, American Journal of Pathology, Philadelphia, PA, US, vol. 166, No. 2, Feb. 2005 (Feb. 2005) p. 625-636.
Zhou et al., Human Cytotrophoblasts Adobt a Vascular Phenotype as They Differentiate, J. Clin. Invest, vol. 99(9), pp. 2139-2151, 1997.
Archived chat from Purdue University dated Feb. 25, 1997; downloaded on Dec. 15, 2010 from purdue.edu/pipermail/cytometry/1997-February/006534.html; 1 page.
Database GEO; "Affymetrix Human Genome U133 Plus 2.0 Array"; XP-002668741, Apr. 19, 2010.
Lipecka et al; "Rescue of ΔF508-CFTR (Cystic Fibrosis Transmembrane Conductance Regulator) by Curcumin: Involvement of the Keratin 18 Network"; The Journal of Pharmacology and Experimental Therapeutica, vol. 317, No. 2, 2006.
Smith, G., Filamentous fusion phage: novel expression vectors that display cloned antigens on the virion surface, Science, 228, 1315-1317, 1985.
Danish Search Report for Application No. PA 2010 01018, dated Jun. 10, 2011.
International Preliminary Report on Patentability for International Application No. PCT/DK2011/050423, dated May 14, 2013.
MSC Research Miltenyi Biotech, MACS Technology—The Complete Solution, 2008.
International Search Report and Written Opinion for International Application No. PCT/DK2011/050423, dated Mar. 8, 2012.
Lu, H. et al., Oral Surgery, Oral Medicine, Oral Pathology, Oral Radiology and Endodontics, Oral and Maxillofacial Pathology, 98(6): 692-697, Dec. 2004.
Ager et al., Retroviral Display of Antibody Fragments; Interdomain Spacing Strongly Influences Vector Infectivity, Hum Gene Ther.,7 (17):2157-64, 1996.
Bhagwat et al., An integrated flow cytometrybased platform for isolation and molecular characterization of circulating tumor single cells and clusters, Scientific Reports, 8:5035, 2018.
Bianchi et al., Erythroid-Specific Antibodies Enhance Detection of Fetal Nucleated Erythocytes in Maternal Blood, Prenatal Diagnosis, vol. 13, pp. 293-300, 1992.
Boder et al., Yeast surface display for screening combinatorial polypeptide libraries, Nat. Biotechnol., 15(6):553-7, 1997.
Brinch et al., Identification of circulating fetal cell markers by micorarray analysis, Prenatal Diagnosis, 32, 742-751, 2012.
Buchholz et al., In vivo selection of protease cleavage sites from retrovirus display libraries, Nat Biotechnol., 16(10):951-4, 1998.
Carlino et al., Recruitment of circulating NK cells through decidual tissues: a possible mechanism controlling NK cell accumulation in the uterus during early pregnancy, Blood, vol. 111, No. 6, pp. 3108-3115, 2008.
Carter et al., High Level *Escherichia coli* Expression and Production of Bivalent Humanized Antibody Fragment, Biotechnology (NY), 10(2):163-7, 1992.
Christensen et al., Studies on the isolation and identification of fetal nucleated red blood cells in the circulation of pregnant women before and after chorion villus sampling, Fetal Diagnosis and Therapy, vol. 18, No. 5, Sep. 2003, 376-384, XP008106278.
Cirigliano et al., Rapid prenatal diagnosis of common chromosone aneuploidies by QF-PCR. Assessment on 18,000 consecutive clinical samples, Molecular Human Reproduction, 10(11): 839-846, 2004.
Cumber et al., Comparative Stabilities In Vitro and In Vivo of a Recombinant Mouse Antibody FvCys Fragment and a bisFvCys Conjugate, J Immunol., 1;149(1):20-6, 1992.
Curtis et al., Flow cytometric methods for prenatal and neonatal diagnosis, Journal of Immunological Methods, 363, 198-209, 2011.
Davydova et al., Culture of human amniotic fluid stem cells in 3D collagen matrix, Cell and Tissue Biology, vol. 5(4);2011; pp. 339-345.

(56) References Cited

OTHER PUBLICATIONS

De Souza et al., Coexpression of cytokeratin and vimentin in mice trophoblastic giant cells, Tissue &Cell; vol. 33, No. 1, pp. 40-45, 2001.
Delsol et al., Antibody BNH9 detects red blood cell-related antigens on anaplastic large cell (CD30+) lymphomas, British Journ of Cancer, vol. 64(2); 1991; pp. 321-326.
D'Souza et al., A Comparison of the Choice of Monoclonal Antibodies for Recovery of Fetal Cells From Maternal Blood Using FACS for Noninvasive Prenatal Diagnosis of Hemoglobinopathies, Cytometry Part B (Clinical Cytometry) 76B:175-180, 2009.
Erdem et al., Maternal and fetal plasma endothelin levels in intra-uterine growth restriction: Relation to umbilical artery Doppler flow velocimetry, J Perinatal Med, vol. 31(1), 2003; pp. 52-59.
Francisco et al., Production and flourescence-activated cell sorting of *Escherichia coli* expressing a functional antibody fragment on the external surface, Proc Natl Aad Sci USA, 90(22):10444-8, 1993.
Georgiou et al., Display of heterologous proteins on the surface of microorganisms: From the screening of combinatorial libraries to live recombinant vaccines, Nat. Biotech. 15, 29-34, 1997.
Gold, L., mRNA display: Diversity matters during in vitro selection, Proc Natl Acad Sci USA., 98(9):4825-6, 2001.
Gotherstrom et al., Identification of candidate surface antigens for non-invasive prenatal diagnosis by comparative global gene expression on human fetal mesenchymal stem cells, Mol. Human Reproduction, 16(7):472-480, Mar. 3, 2010.
Greenberg et al., A new antigen receptor gene family that undergoes rearrangement and extensive somatic diversification in sharks, Nature (London) 374, 168-173, 1995.
Griffiths et al., Isolation of high affinity human antibodies directly from large synthetic repetoires, EMBO J., Jul. 15;13(14):3245-60, 1994.
Gussin et al., Culture of endothelial cells isolated from maternal blood using anti-CD105 and CD133, Prenat. Diagn.; vol. 24, No. 3; pp. 189-193, 2004.
Hager et al., The use of a panel of monoclonal antibodies to enrich circulating breast cancer cells facilitates their detection, Gynecologic Oncology, vol. 98, pp. 211-216, 2005.
Hai et al., Application of laser capture microdissection to phage display peptide library screening, Oral Surgery, Oral Medicine, Oral Pathology, Oral Radiology and Endodontics, MOSBY—Year Book, St. Louis, No. US. vol. 98, No. 6, Dec. 2004 (Dec. 2004), p. 692-697.
Hamers-Casterman et al., Naturally ocurring antibodies devoid of light chains, Nature, 363(6428):446-8, 1993.
Hanes et al., In vitro selection and evolution of functional proteins by using ribosome display, Proc. Natl. Acad. Sci., vol. 94, p. 4937-4942, 1997.
Hatt et al., A new marker set that identifies fetal cells in maternal circulation with high specificity, Prenatal Diagnosis, 34, 1-7, 2014.
Hatt et al., Characterization of Fetal Cells from the Maternal Circulation by Microarray Gene Expression Analysis—Could the Extravillous Trophoblasts Be a Target for Future Cell-Based Non-Invasive Prenatal Diagnosis?, Fetal Diagn Ther, 1-10, 2013.
Hemberger et al., Differential Expression of Angiogenic and Vasodilatory Factors by Invasive Trohoblast Giant Cells Depending on Depth of Invasion, Developmental Dynamics 227; pp. 185-191, 2003.
Hengstschläger et al., Fetal cells in the peripheral blood of pregnant women express thymidine kinase: a new marker for detection, FEBS Letters, vol. 404 (2-3), 1997; pp. 299-302.
Ho et al., Identification of endothelial cell genes by combined database mining and microarray analysis, Physiol Genomics 13: 249-262, 2003.
Huie et al., Antibodies to human fertal erythroid cells from a nonimmune phage antibody library, Proceedings of the national academy of Sciences of USA, National Academy of Science, Washington, DC, US, vol. 98, No. 5, Feb. 27, 2001 (Feb. 27, 2001) p. 2682-2687.
Jan et al., NanoVelcro Rare-Cell Assays for Detection and Characterization of Circulating Tumor Cells, Adv Drug Deliv Rev., 125: 78-93, 2018.
Jensen et al., Functional improvement of antibody fragments using a novel phage coat protein II fusion system, Biochem Biophys Res Commun 298, 566-573, 2002.
Khosrothehrani et al., Multi-lineage potential of fetal cells in maternal tissue: a legacy in reverse, J Cell Sci, 118 (Pt8): 1559-63, 2005.
Koumantaki et al., Microsatellite analysis provides efficient confirmation of fetal trophoblast isolation from maternal circulation, Prenatal Diagnosis, vol. 21; 2001; pp. 566-570.
Kristensen et al., Proteolytic selection for protein folding using filamentous bacteriophages, Fold Des. 3, 321-328, 1998.
Kuka et al., A method for high purity sorting of rare cell subsets applied to TDC, J Immunol Methods, 2013.
Kunisaki et al., Fetal Cartilage Engineering from Amniotic Mesenchymal Progenitor Cells, Stem Cells and Development, vol. 15(2), pp. 245-253, 2006.

\* cited by examiner

A)  B)  C)  D)  E)

A)   B)   C)   D)   E)   F)   G)

A)

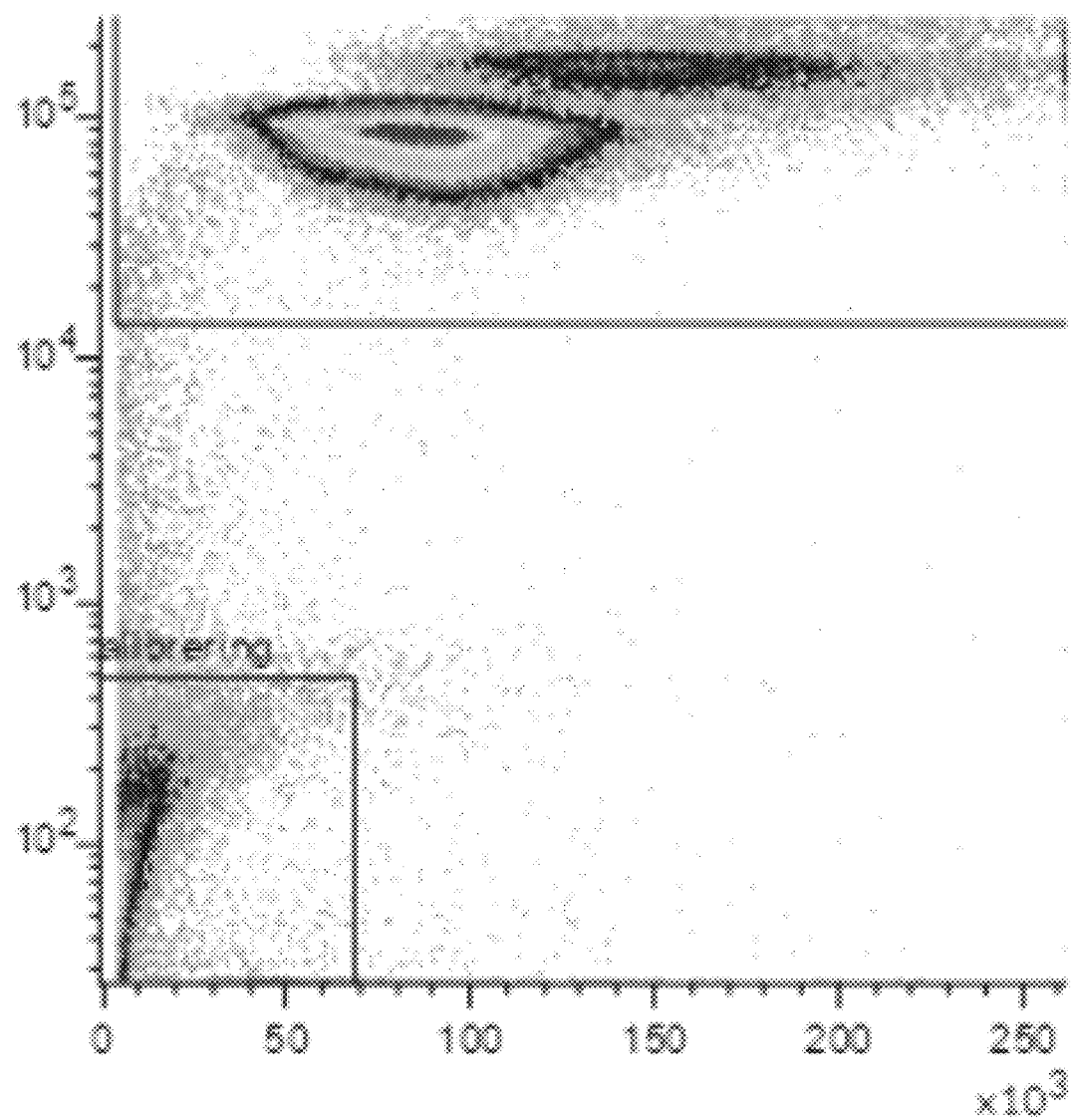
Fig. 8, cont.

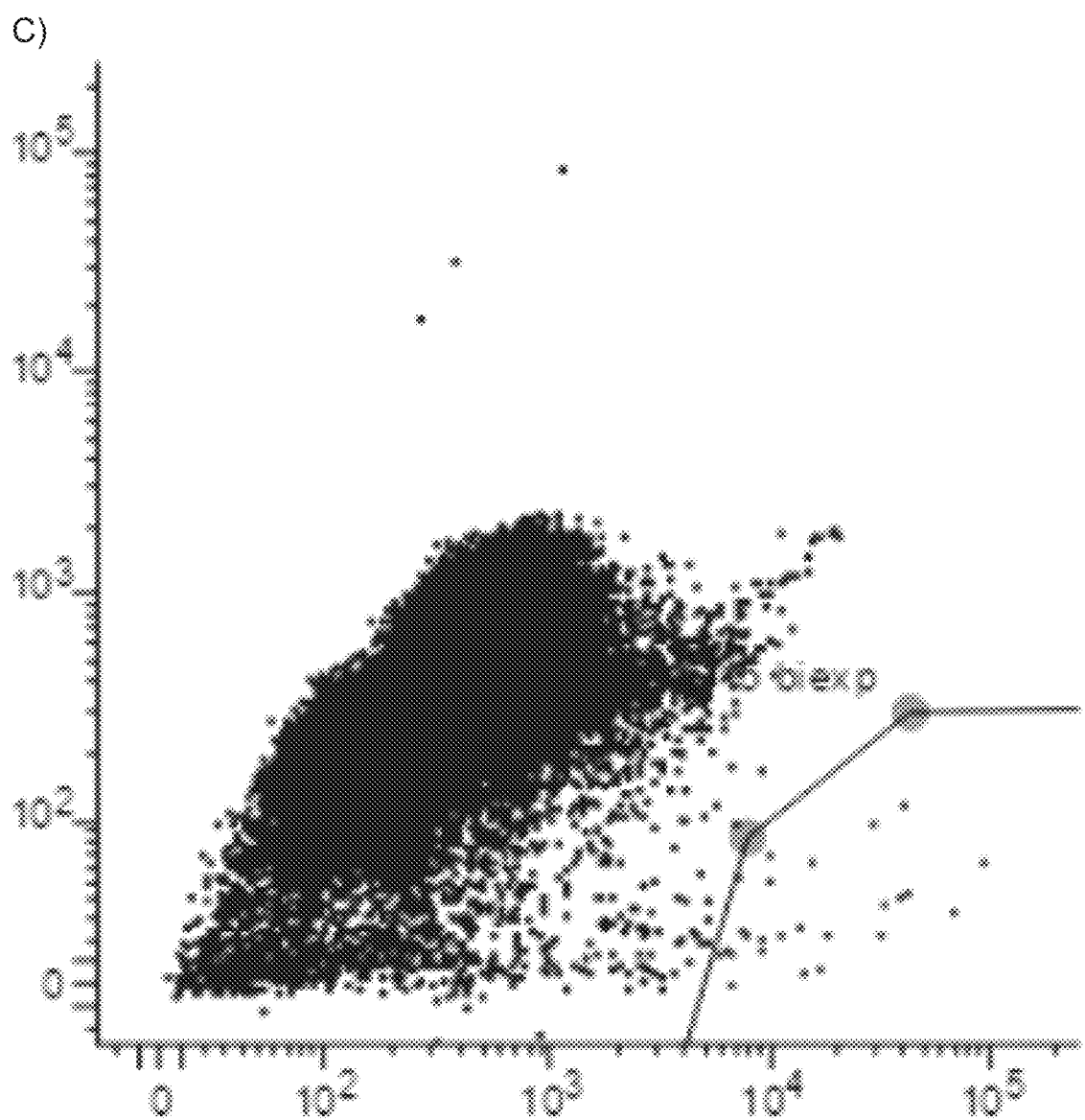
Fig. 8, cont.

A)

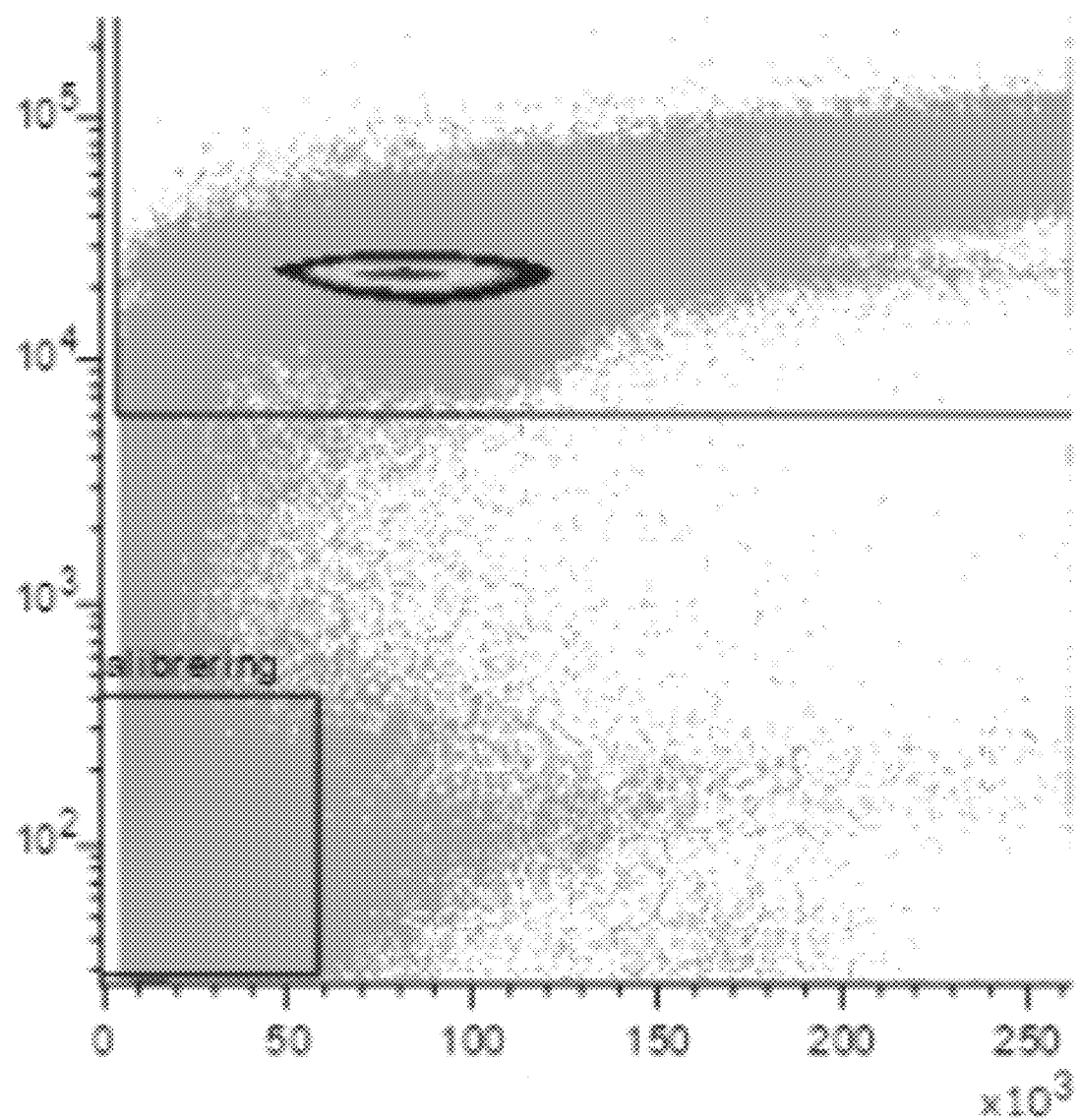
Fig. 9, cont.

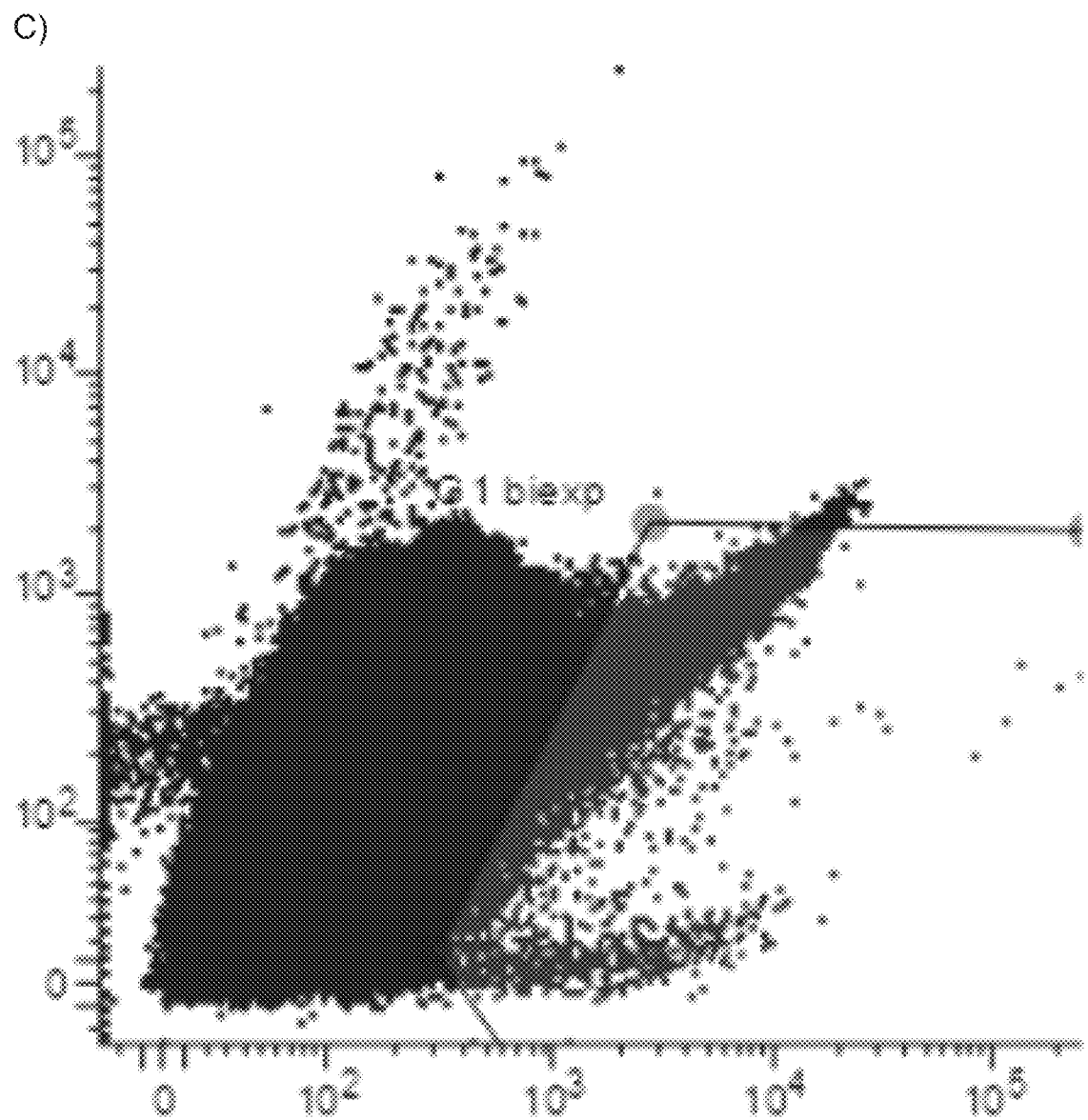
Fig. 9, cont.

A)

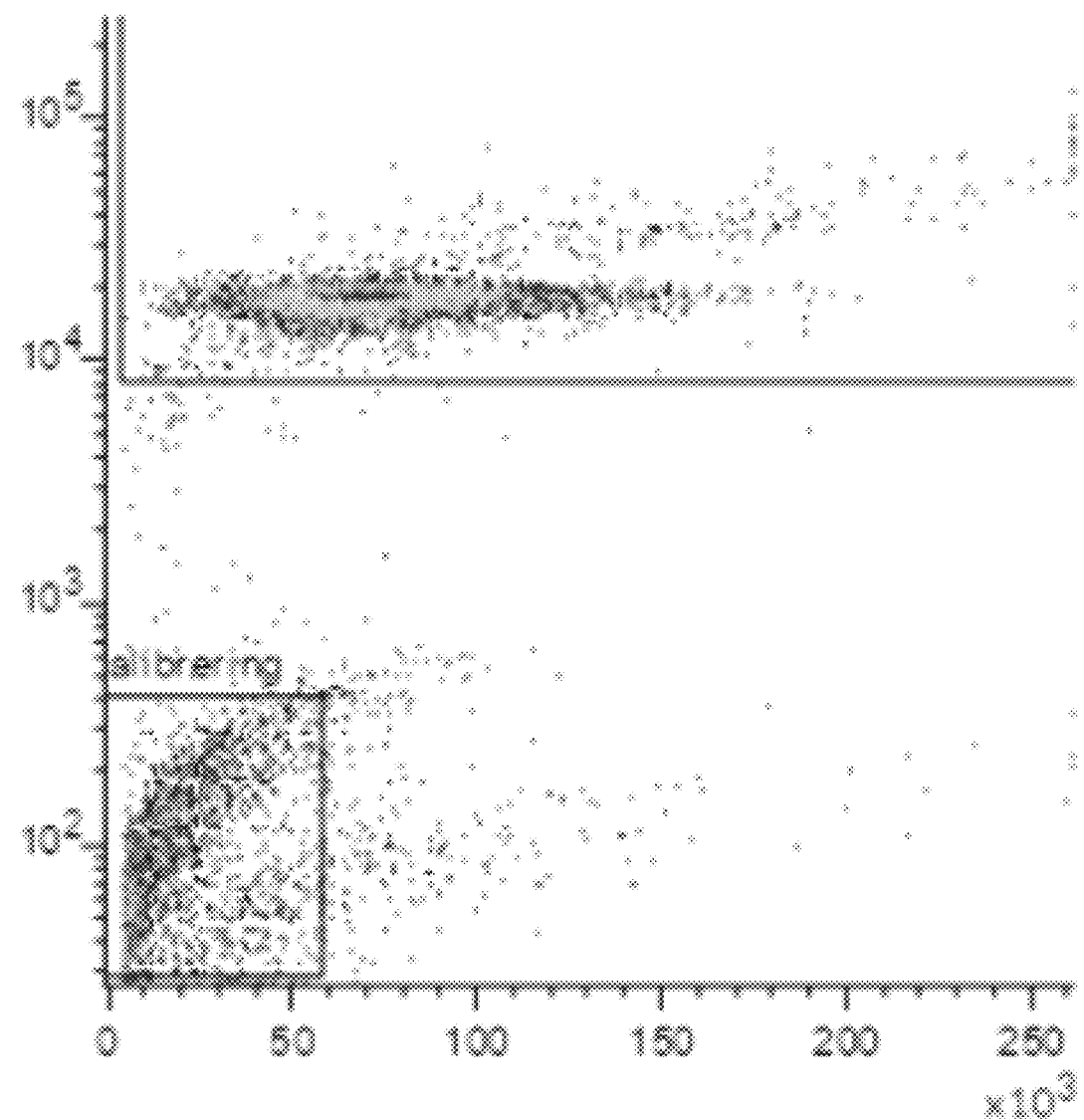
Fig. 10, cont.

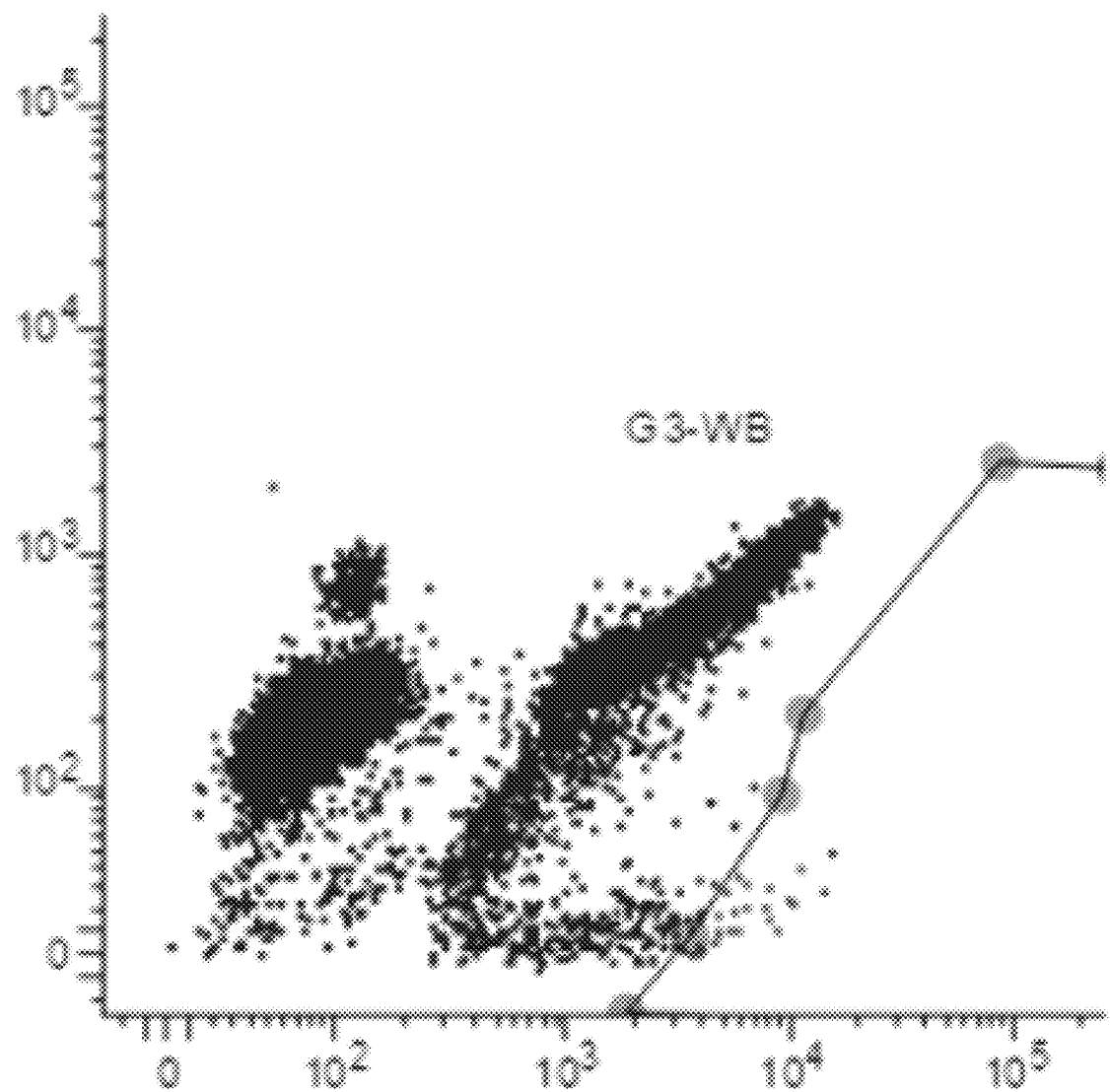
Fig. 10, cont.

A)

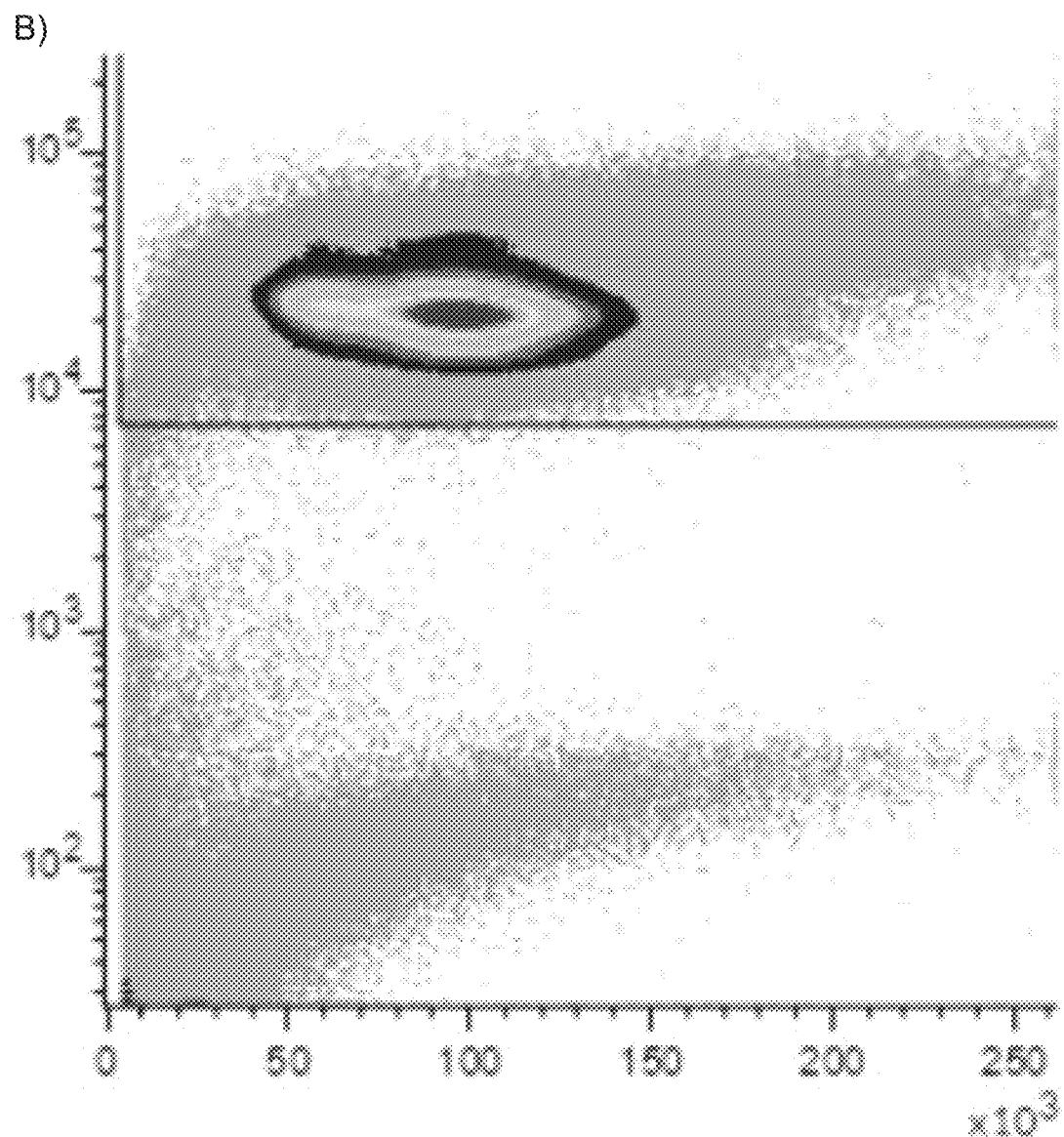
Fig. 11, cont.

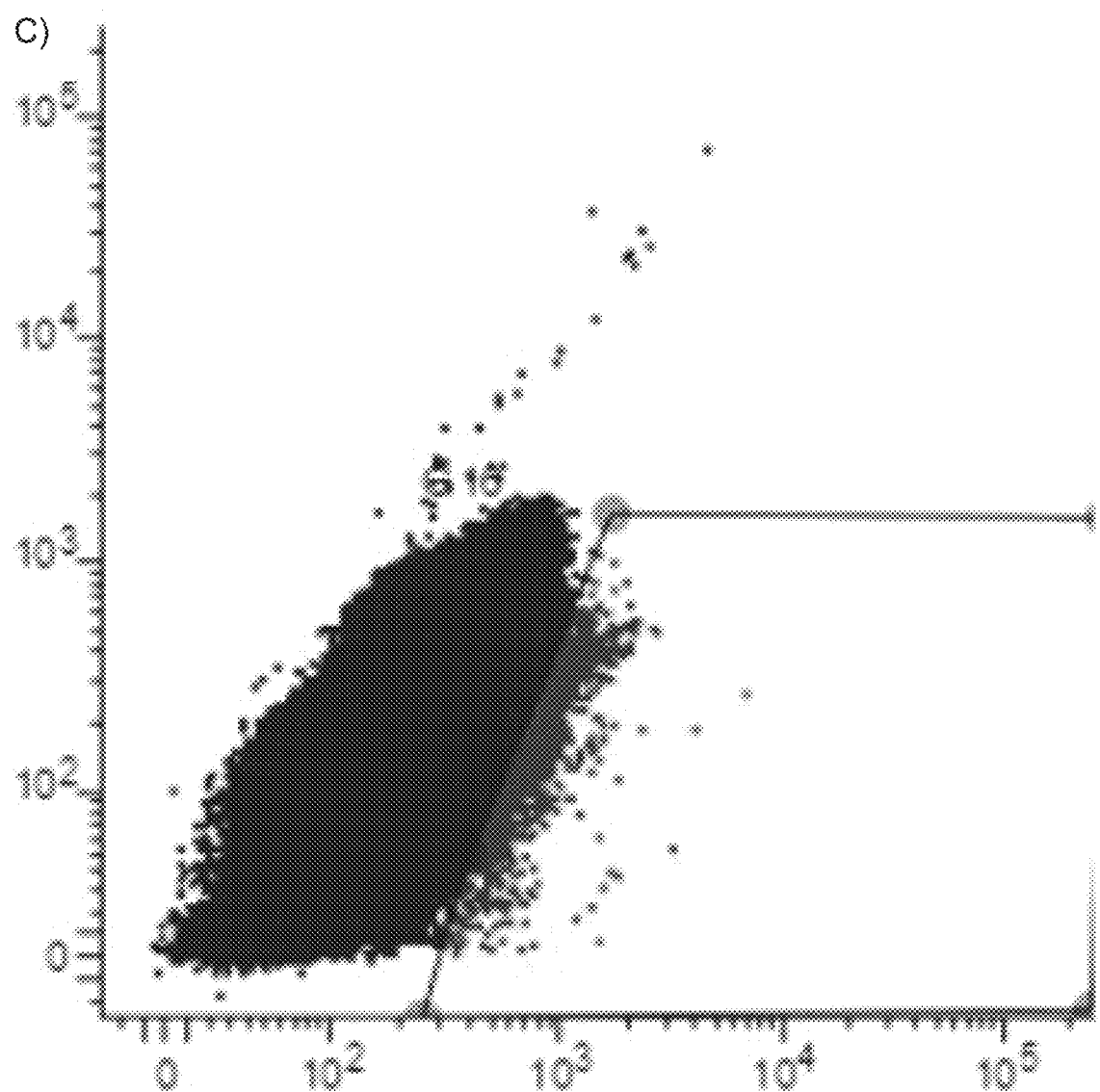
Fig. 11, cont.

A)

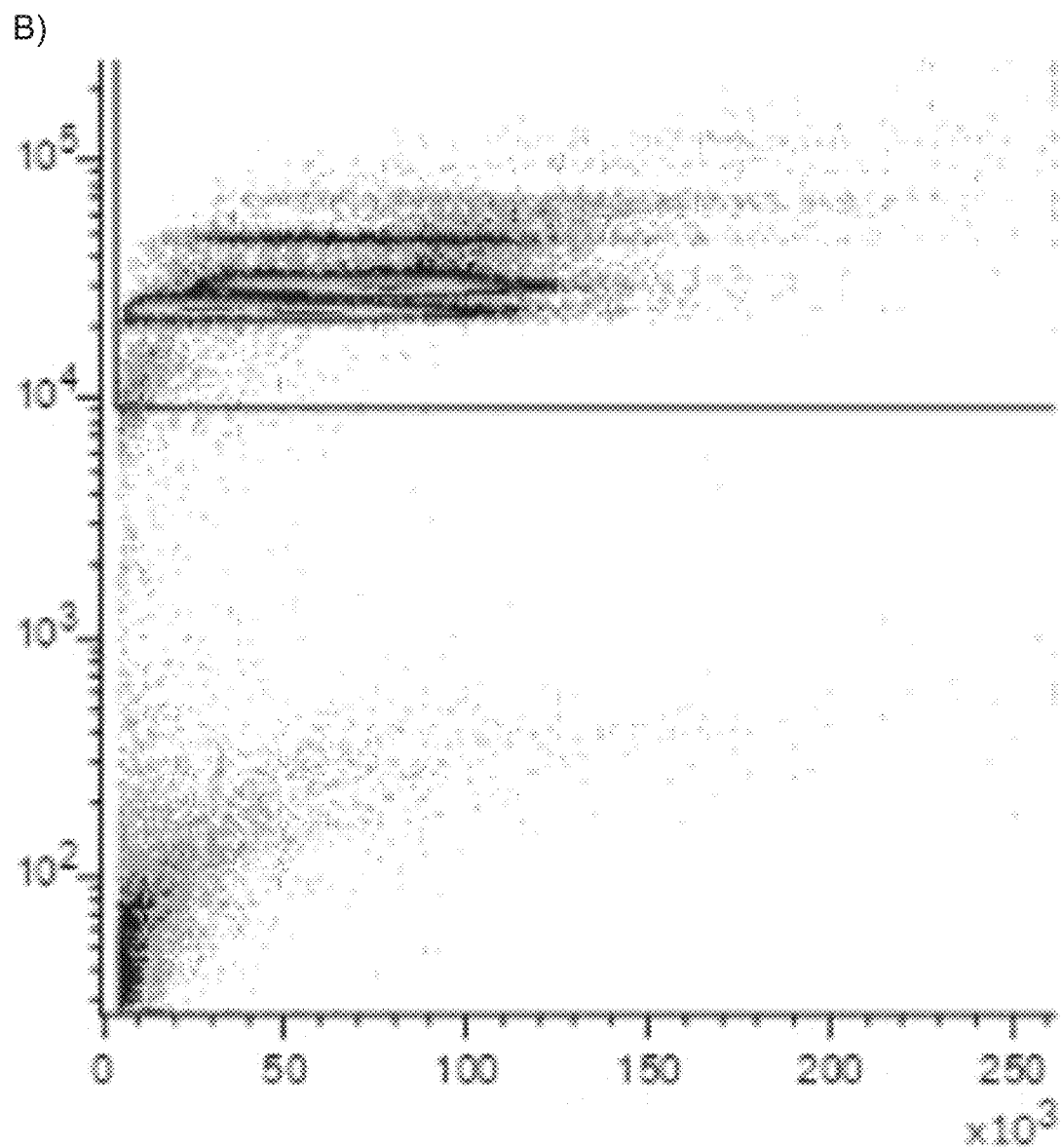
Fig. 12, cont.

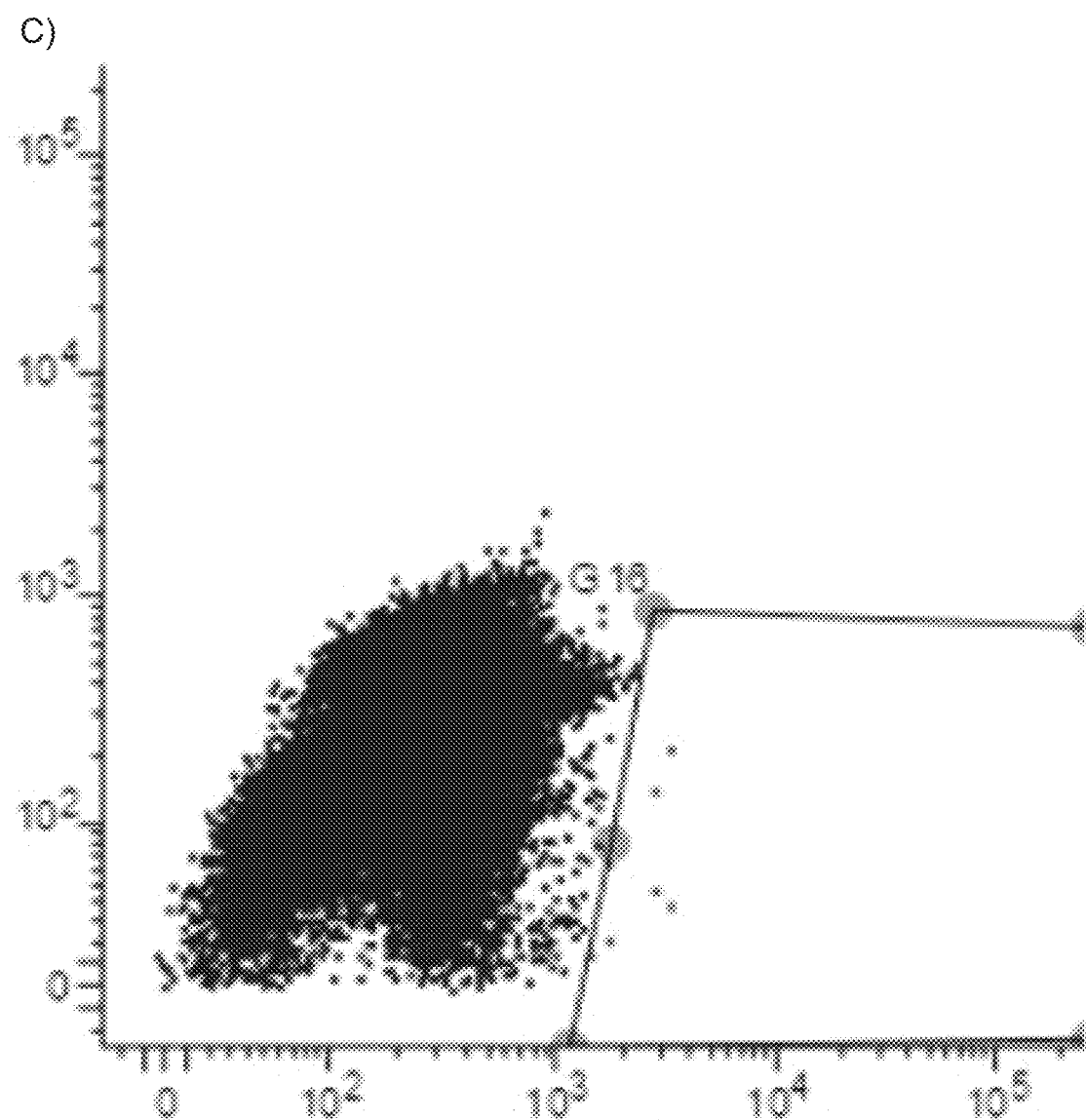
Fig. 12, cont.

A)

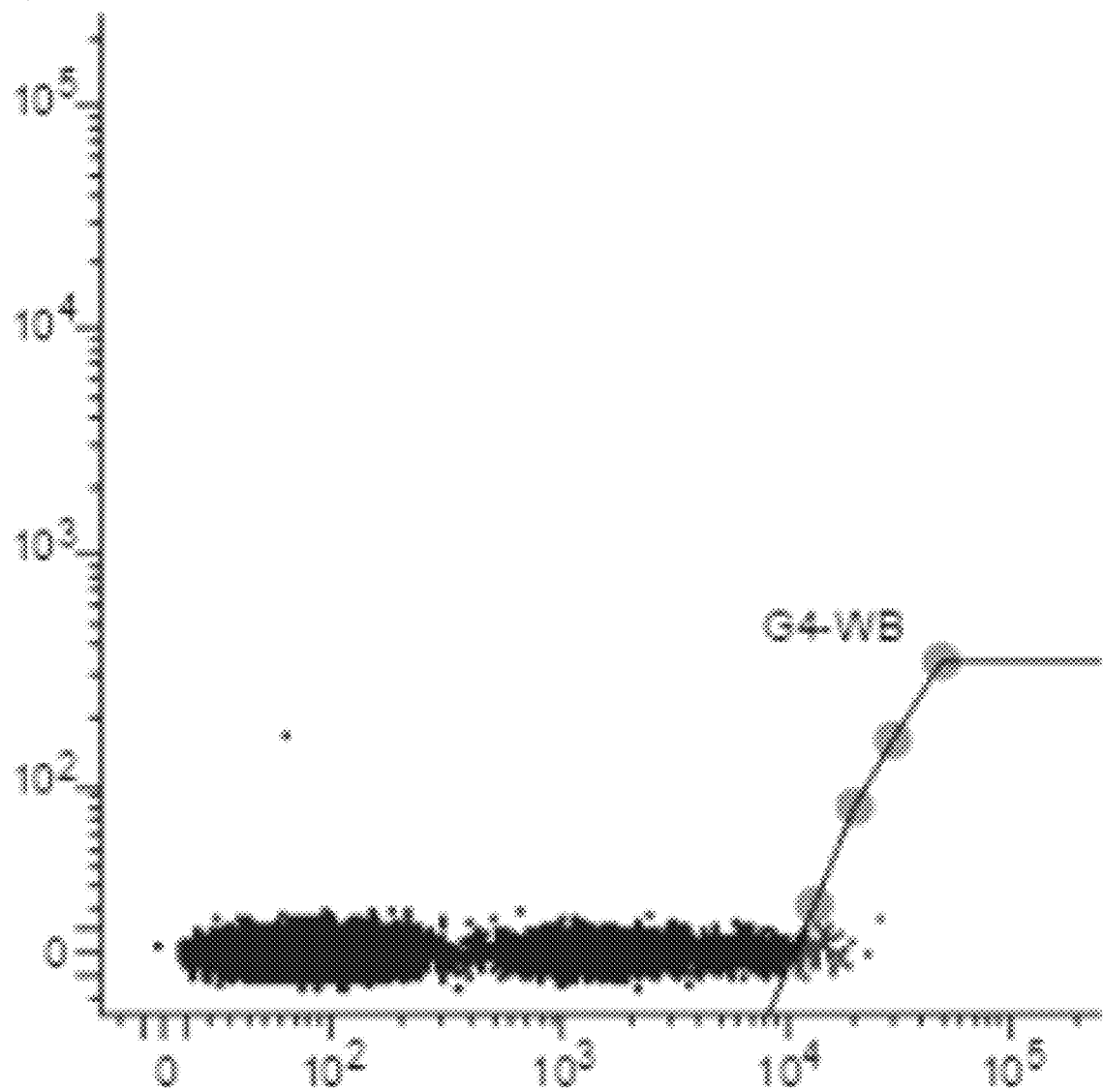
Fig. 13, cont.

A)

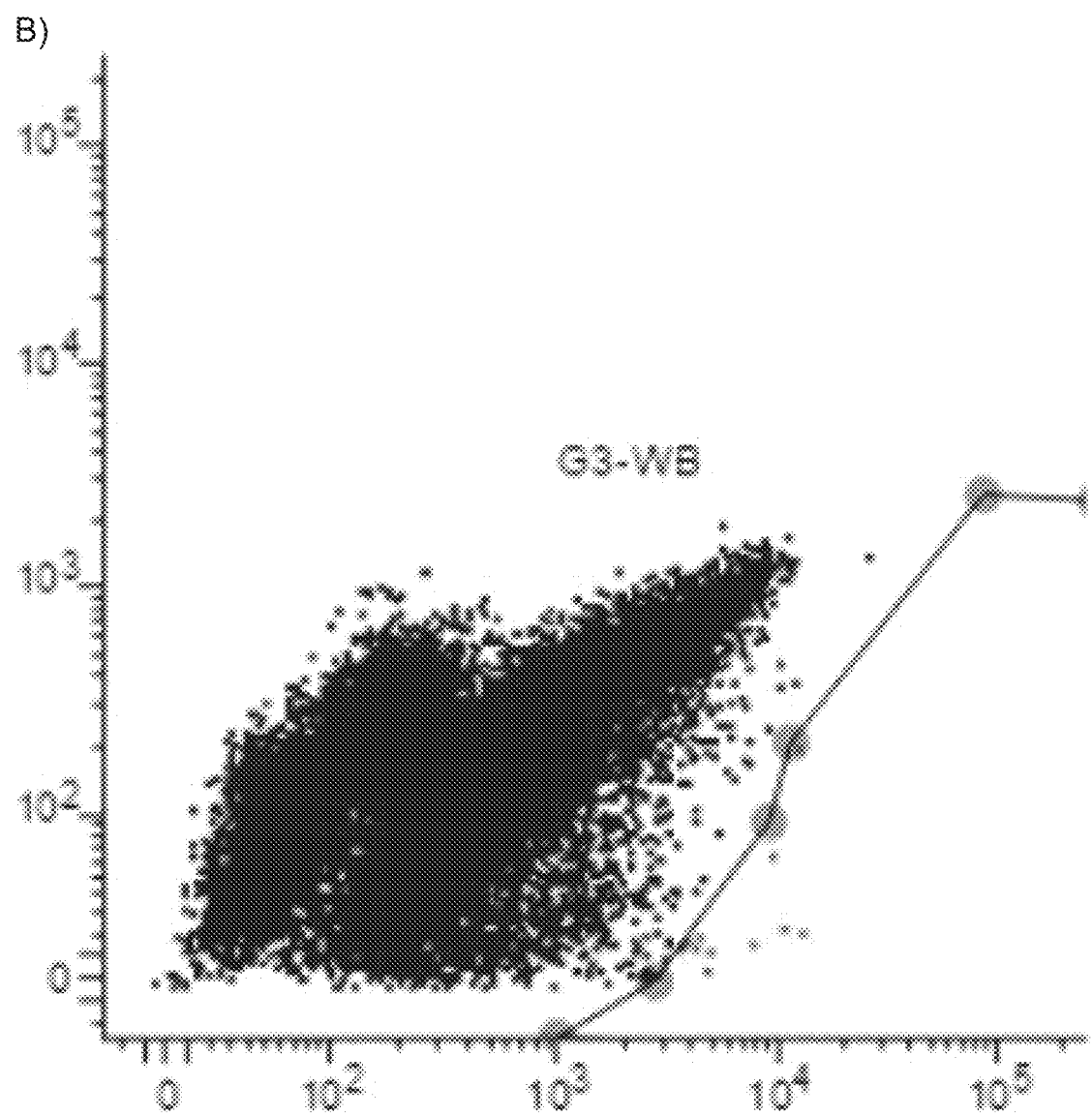
Fig. 14, cont.

ISOLATION OF FETAL CELLS USING FACS

REFERENCE TO RELATED APPLICATIONS

This application is a continuation of PCT International Application No. PCT/EP2020/065832, filed Jun. 8, 2020, which claims priority to European Patent Application No. 19179087.2, filed Jun. 7, 2019. The entire content of both of which is incorporated herein by reference.

TECHNICAL FIELD

The present invention relates to automated methods for isolating fetal cells from a sample, such as a blood sample, derived from a pregnant woman. The isolated fetal cells can be used for identifying genetic abnormalities in the fetal DNA.

BACKGROUND

During pregnancy fetal cells from the placenta can invade the maternal blood circulation. Most of these fetal cells originate from the placenta, and are trophoblasts, endovascular trophoblasts or extravillous trophoblasts (EVTs). These fetal cells that invade the maternal circulation display both endothelial and epithelial characteristics. The process by which epithelial trophoblasts change characteristics and invade the maternal circulation is called Epithelial-Mesenchymal Transition (EMT).

EMT is a process by which epithelial cells gradually lose their epithelial characteristics and acquire a mesenchymal-like phenotype. EMT has been described in early embryogenesis where migration and transient dedifferentiation of embryonic epithelial cells are required for the formation of e.g. the neural tube.

By utilizing a mesoderm marker (i.e. an endothelial marker) as a positive selection marker the fetal cells present in a very low number in a maternal blood sample are enriched together with some maternal cells. Positive identification of the fetal cells is subsequently done by contacting the enriched cells with an epithelial marker thereby utilizing the EMT phenomenon. None of the normal maternal cells present in a blood sample is expressing any epithelial markers.

In prior art methods as illustrated in FIG. 2A, maternal blood samples have been subjected to processing followed by enrichment to get rid of the majority of maternal cells. Subsequently, cells have been stained with fluorescently labelled maternal and fetal markers and scanned on a slide. The latter process is tedious and time-consuming considering the extremely low frequency of fetal cells in a maternal blood sample.

SUMMARY

In one aspect the invention relates to a method of isolating fetal cells from a biological sample of a pregnant woman, said method comprising the steps of
a. providing a biological sample from said pregnant woman, the biological sample comprising a cellular fraction,
b. contacting cells comprised in said cellular fraction with one or more fluorescent labelling agents directed against at least one fetal cell epithelial marker and/or endothelial marker,
c. sorting said cells by Fluorescence-activated cell sorting (FACS) based on detection of said one or more fluorescent labelling agents bound to cells, and
d. identifying fetal cells among said sorted cells comprising a step of assigning a fetal origin classifier to individual sorted cells.

The inventors have made the surprising observation that it is possible to perform single cell sorting using FACS and subsequently identify those cells that have a high probability of being fetal by simply analysing the output from the FACS in terms of a number of parameters such as scatter and signals from one or more fluorescently labelled antibodies. The output can be combined to a classifier, which may be numeric score or binary. Using methods of the invention, the inventors have developed a method with a very high likelihood of identifying fetal cells among the sorted cells.

The advantages over prior art methods are illustrated in FIG. 1, the main advantage being that the process can be fully automated and that it requires no picking of cells identified as probable fetal cells.

The identified cells can be verified as fetal cells by genetic analysis and can be further used for identifying genetic abnormalities in the cells.

In a further aspect the invention relates to a method of determining a genetic abnormality in a fetus said method comprising the steps of:
a. Obtaining one or more fetal cells isolated by a method of the invention, and
b. Detecting one or more genetic markers associated with said genetic abnormality in the genome of said fetal cell.

Figure 1:
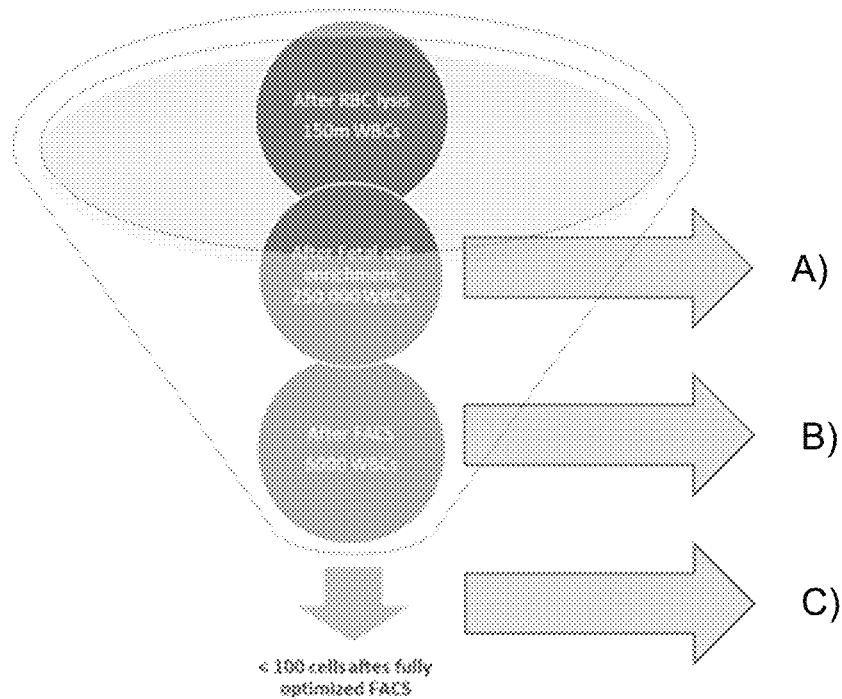
FIG. 1

Rationale for using FACS for fetal cell enrichment and isolation. A)=Fetal cell access after this step is laborious and makes the process throughput low. B)=Fetal cell access after this step is faster, and with less risk of maternal cell contamination. However, still requires human intervention. C)=No physical picking of fetal cells. 1 cell per 96 well plate followed by single cell analysis.

FIG. 2

Fetal cell enrichment without FACS (A) and with FACS (B)

A.1 and B.1=sampling, A.2 and B.2=blood processing, A.3 and B.3=selection, enrichment and staining, A.4. and B.5=scanning, and "picking" fetal cells and B.4=FACS.

FIG. 3

X and Y coordinates of Gate 1 on the FACS plot for Alexa Fluor 488 (X-axis) (CK antibodies) and PE (Y-axis) (CD14+CD45). The two of the five coordinates that connect the diagonal line are not fixed but have a range in the x and y axis.

FIG. 4

Single cell sorting using FACS and analysing them using STR analysis. A)=sampling, B)=blood processing, C=selection, enrichment and staining, D)=FACS and E)=ABI 3500 (STR analysis)

FIG. 5

X and Y coordinates of Gate G7 on the FACS plot for Alexa Fluor 488 (X-axis) (CK antibodies) and PE (Y-axis) (CD14+CD45). Gate G7 was used to individually sort single cells in individual tubes.

FIG. 6

Compiled data from STR analysis on single sorted cells. The percentages in the figure are average of the individual percentages from each sample. A)=maternal cells, B)=fetal cells, C)=fetal+maternal cells, D)=empty and E)=other contamination

FIG. 7

Workflow of a complete implementation with fetal cell enrichment, identification, and analysis after single sorting cells using FACS. A)=sampling, B)=blood processing, C=selection, enrichment and staining, D)=FACS, E)=Whole Genome Amplification (WGA), F)=ABI 3500 (STR analysis) and G)=Array comparative genome hybridization.

FIG. 8

Gating strategy. A) All events, FSC-A (X-axis) and SSC-A (Y-axis). Events (debris) with high SSC values were excluded. B) Low SSC events, FSC-A (X-axis) and Hoechst (Y-axis). The remaining cells were then gated for Hoechst$^+$ cells. C) Hoechst events, AF488 (X-axis) and AF555 (Y-axis). From the Hoechst$^+$ fraction, CK$^+$CD45$^-$CD14$^-$ cells were single cell sorted.

FIG. 9

Gating strategy for the first sort. A) All events, FSC-A (X-axis) and SSC-A (Y-axis). Events (debris) with high SSC values were excluded. B) Low SSC events, FSC-A (X-axis) and Hoechst (Y-axis). The remaining cells were then gated for Hoechst$^+$ cells. C) Hoechst events, AF488 (X-axis) and AF555 (Y-axis). From the Hoechst$^+$ fraction, CK$^{medium-to-high}$CD45$^-$CD14$^-$ cells were bulk sorted as an enrichment step.

FIG. 10

Gating strategy for the second sort. A) All events, FSC-A (X-axis) and SSC-A (Y-axis).

Events (debris) with high SSC values were excluded. B) Low SSC events, FSC-A (X-axis) and Hoechst (Y-axis). The remaining cells were then gated for Hoechst$^+$ cells. C) Hoechst events, AF488 (X-axis) and AF555 (Y-axis). From the Hoechst$^+$ fraction, CK$^{high}$CD45$^-$CD14$^-$ cells were single cell sorted.

FIG. 11

Gating strategy for the first sort for sample 3091-B. A) All events, FSC-A (X-axis) and SSC-A (Y-axis). Events (debris) with high SSC values were excluded. B) Low SSC events, FSC-A (X-axis) and Hoechst (Y-axis). The remaining cells were then gated for Hoechst$^+$ cells. C) Hoechst events, AF488 (X-axis) and AF555 (Y-axis). From the Hoechst$^+$ fraction, CD141+CD105$^{medium-to-high}$CD45$^-$CD14$^-$ cells were bulk sorted as an enrichment step.

FIG. 12

Gating strategy for the second sort for sample 3091-B. A) All events, FSC-A (X-axis) and SSC-A (Y-axis). Events (debris) with high SSC values were excluded. B) Low SSC events, FSC-A (X-axis) and Hoechst (Y-axis). The remaining cells were then gated for Hoechst$^+$ cells. C) Hoechst events, AF488 (X-axis) and AF555 (Y-axis). From the Hoechst$^+$ fraction, CD141+CD105$^{high}$CD45$^-$CD14$^-$ cells were single cell sorted.

FIG. 13

Gating strategy for the second sort A) Low SSC events, AF488 (X-axis) and AF555 (Y-axis). The second sorting for sample AAL302-B. No Hoechst, CD45 or CD14 was added. B) Low SSC and Hoechst events, AF488 (X-axis) and AF555 (Y-axis). The second sorting for sample AAL302-A. Hoechst was added but no CD45 or CD14.

FIG. 14

Gating strategy for the second sort A) Low SSC and Hoechst events, AF488 (X-axis) and AF555 (Y-axis). The second sorting for sample K0381 where no CD45 was added. B) Low SSC and Hoechst events, AF488 (X-axis) and AF555 (Y-axis). The second sorting for sample K0380 where no CD14 was added.

DETAILED DESCRIPTION

The challenges associated with isolation on fetal cells from a maternal blood sample are illustrated in FIG. 1. Typically, a blood sample of 30 mL contains approximately 150 mio cells after lysis of the red blood cells. These can be enriched for fetal cells using enrichment methods as herein described. This may result in a sample with approximately 250,000 cells. Among these there are very few fetal cells so manual screening for fetal cells or picking of cells from a slide is a very laborious method.

One example of such method is illustrated in the flow diagram of FIG. 2A, where a blood sample is taken, the sample is processed and subjected to enrichment. The remaining cells are spotted on a slide and scanned and picked in a microscope using a combination of manual and semi-automatic procedures.

One of our examples show, that Fluorescence Activated Cell Sorting (FACS) can be used to enrich this population even further for fetal cells to bring the number of cells to be examined individually still down to several thousand cells. A flow diagram illustrating this method is found in FIG. 2B.

The inventors have made the surprising finding that it is possible to single sort fetal cells from an enriched maternal blood sample, therefore the invention also relates to a method of prenatal diagnostics comprising the steps of:

1. providing a blood sample from a woman carrying a fetus, said blood sample comprising a cellular fraction,
2. enriching said sample for fetal cells,
3. contacting said sample with at least one fluorescent labelling agent selected from each of the groups:
    i. fluorescent labelling agent directed against the nucleus,
    ii. fluorescent labelling agent directed against a maternal cell marker, and
    iii. fluorescent labelling agent directed against a fetal cell marker
4. single cell sorting at least one fetal cell on a fluorescence activated cell sorter (FACS) from said enriched sample based on:
    i. positive selection of said fluorescent labelling agent directed against a fetal cell marker,
    ii. positive selection of said fluorescent labelling agent directed against the nucleus, and
    iii. negative selection of said fluorescent labelling agent directed against a maternal cell marker
5. identifying said at least one fetal trophoblast among said sorted cells, comprising a step of assigning a fetal origin classifier to individually sorted cells by obtaining a genotype from said fetal trophoblast, and
6. diagnosing the phenotype of the fetus.

The purpose of enrichment with MACS is to reduce the number of cells loaded into the FACS machine (cf FIG. 1 showing that enrichment reduces the number of cells from approx. 150 mio to approx. 250.000). Performing the MACS enrichment is not necessary as shown in the examples which demonstrate that the identification of fetal cells from an unenriched sample is possible. This just results in a much higher number of events in the FACS machine. More specifically, example 3 shows that FACS can be used to enrich a sample for fetal cells.

Magnetic-activated cell sorting (MACS) is a method for separation of various cell populations depending on their surface antigens (CD molecules).

In other embodiments MACS is used on intracellular target, such as for example with microbeads against epithelial markers such as cytokeratin microbeads.

Miltenyi Biotec's MACS system uses superparamagnetic nanoparticles and columns. The superparamagnetic nanoparticles are of the order of 100 nm. They are used to tag the targeted cells in order to capture them inside the column.

The column is placed between permanent magnets so that when the magnetic particle-cell complex passes through it, the tagged cells can be captured. The column consists of steel wool which increases the magnetic field gradient to maximize separation efficiency when the column is placed between the permanent magnets.

Magnetic-activated cell sorting is a commonly used method often in combination with microbeads which are magnetic nanoparticles conjugated to antibodies which can be used to target specific cells. Magnetic-activated cell sorting can be used to enrich a cell population for desired cells. The magnetic nanoparticles can be conjugated directly to a labelling agent. The magnetic nanoparticles can also be conjugated to another agent capable of binding the labelling agent (secondary labelling).

If MACS is chosen as the enrichment step it is preferred that this step is preceded by a step of contacting cells comprised in the cellular fraction with at least one magnetic labelling labelled agent directed against a fetal cell marker.

In one embodiment of the disclosure, the sample is enriched for fetal cells by selecting cells labelled with a labelling agent specific for one or more endothelial markers. Examples of endothelial markers are described further herein below.

In one embodiment of the disclosure, the sample is enriched for fetal cells by selecting cells labelled with a labelling agent specific for one or more epithelial markers. Examples of epithelial marker are described further herein below.

The epithelial marker(s) may be used for enrichment of fetal cells in the sample. Enrichment may be done using immobilization of the antibodies to a solid surface.

One preferred embodiment of enrichment is MACS, where the labelling agent comprises antibodies immobilized on magnetic beads.

Cell sorting is a method used to purify cell populations based on the presence or absence of specific physical characteristics. In flow cytometers with sorting capabilities, the instrument detects cells using parameters including cell size, morphology, and protein expression, and then droplet technology to sort cells and recover the subsets for post-experimental use.

Flow cytometry cell sorters have a collection system unlike flow cytometry analyzers. The collection process starts when a sample is injected into a stream of sheath fluid that passes through the flow cell and laser intercepts. The stream then carries the cell through a vibrating nozzle. The disturbance in the stream causes it to break into a droplet containing ideally one cell. An electrical charging ring is placed just at the point where the stream breaks into droplets. A charge is placed on the ring based immediately prior to fluorescence intensity being measured, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

If collected under sterile conditions, the sorted cells can be further cultured, manipulated, and studied.

The sorting on such a FACS can be both single cell sorting and bulk sorting, cells that are discarded and not displaying the given thresholds are.

Gates are set to define how the FACS instrument shall sort cells. Cells that fall within the settings are sorted and cells that fall outside the gates are either sorted for later investigations or discarded. Depending on how the FACS instrument is setup by the user, the sorting can be either a bulk sorting or a single cell sorting. A bulk sorting results in cells falling within the given gate settings to be collected in the same tube. Single cell sorting results in cells falling within the given settings to be individually sorted into collection tubes. The single cell sorting is often more time consuming than a bulk sorting, as exemplified in example 5. As a FACS instrument is capable of sorting several 1000 cells/second, the different setups can vary much depending on the experiment. When sorting into single cell compartments one needs to have a low output, such as a 96 well plate. On the contrary when using bulk sorting, one can sort several thousand cells/tube.

In an embodiment of the invention, a bulk sorting is used to enrich a sample. In another embodiment, single cell sorting is used to single cell sort cells, such as for example into single cell compartments.

Depending on the gating strategy of an experiment, one can reduce the amount of agents that needs to be applied to the sample as well as the time used for an experiment, by using a bulk sorting at first followed by a single sorting. Such parameters suitably may include quantifying forward scatter, side scatter and fluorescence emitted from fluorophores excited by lasers within the flow cytometer.

Forward scatter is understood as the disturbance in the direction of the lightpath the object causes and typically correlates with the size of the cell.

Side scatter is understood as the light reflected away from the direction of the lightpath and typically correlates with the amount of granules in the way of the lightpath.

Emitted fluorescence is quantified when a light source such as a laser excites fluorophores present on the sample and passes through filters known to the person skilled in the art to fit with given lasers and fluorophores. Given a fluorophore with a specific excitation wavelength and emission wavelength, the skilled person is able to select a light source with suitable wavelength, and suitable excitation and emission filters.

When the parameters have been measured by the flow cytometer the cells may be sorted. Suitably this is done by sorting each cell into a separate compartment. The sorted cells are preferably cells that express at least one epithelial marker and/or endothelial marker and do not express at least one cell marker specific for blood cells. Examples of how to select cells for sorting can be found in the examples where specific Gates are selected for sorting. The Gate is chosen to maximize the likelihood of sorting fetal cells while keeping the number of sorted cells relatively low. The remaining—non-sorted—cells are discarded because they are not expected to contain any fetal cells.

In another preferred embodiment, the FACS is used for enrichment, where preferably the sorted cells are collected in a tube before the, now enriched, sample is single cell sorted on the FACS.

In one embodiment, the sample is enriched on a FACS based on the signal from an epithelial marker.

In another embodiment, the sample is enriched on a FACS based on the signal from an endothelial marker.

Thus, If FACS is chosen as the enrichment step it is preferred that this step is preceded by a step of contacting cells comprised in the cellular fraction with at least one fluorescent labelled agent directed against a fetal cell marker.

Following the enrichment step, the single cell sorting by FACS is performed. In a preferred embodiment, cells positive for the at least one epithelial marker and being negative or low for said at least one blood cell marker are sorted into single cell compartments. This is exemplified in FIG. 8, C).

In another preferred embodiment, cells are sorted into single cell compartments based on a positive signal for a fetal marker, a nucleus marker and a negative signal for a maternal marker. This is exemplified in FIG. 8, B) and C).

In a preferred embodiment, the sample is sorted by using the same gating strategy for the enrichment and the single cell sorting.

In another embodiment, the sample is sorted by using the same gating strategy for the enrichment and the single cell sorting, with a difference in the size of the gate for the enrichment and the single cell sorting.

The isolation methods herein disclosed preferably use fluorescent labelling agents to selectively label fetal and maternal cells. In one embodiment, the methods rely on using endothelial, epithelial and blood cell markers to distinguish the fetal cells from the maternal cells and may further use a nucleus stain to distinguish cells from debris.

In other embodiments, the labelling agents are magnetic labelling agents, such as they can be immobilized in methods used in the invention, such as MACS.

The fetal marker may be one or more epithelial markers, such as one or more cytokeratins (CKs). Cytokeratins are keratin proteins found in the intracytoplasmic cytoskeleton of epithelial tissue. Cytokeratins vary in size from 40-68 kDa. They are an important component of intermediate filaments, which help cells resist mechanical stress. Expression of these cytokeratins within epithelial cells is largely specific to particular organs or tissues. Cytokeratins are selected from the group consisting of Human Cytokeratin 1 CK1, Human Cytokeratin 2 CK2, Human Cytokeratin 3 CK3, Human Cytokeratin 4 CK4, Human Cytokeratin 5 CK5, Human Cytokeratin 6 CK6, Human Cytokeratin 7 CK7, Human Cytokeratin 8 CK8, Human Cytokeratin 9 CK9, Human Cytokeratin 10 CK10, Human Cytokeratin 13 CK13, Human Cytokeratin 14 CK14, Human Cytokeratin 15 CK15, Human Cytokeratin 16 CK16, Human Cytokeratin 17 CK17, Human Cytokeratin 18 CK18, Human Cytokeratin 19 CK19.

In preferred embodiments, the cytokeratin is CK7, CK8, CK18, CK19 or a combination thereof.

In one embodiment, the labelling agent against the epithelial markers is a pan CK labelling agent. A pan CK labelling agent is a labelling agent targeting several cytokeratins at once. In one embodiment, the pan CK labelling agent is targeting cytokeratins with a molecular weight of 58, 56, 52, 60, 51, 48 and 68 kDa.

In preferred embodiments, the labelling agents is a combination of agents targeting CK7, CK8, CK18, CK19 as wells as a pan CK labelling agent.

There is no need to discriminate between different cytokeratin markers, therefore suitably the fluorescent labelling agents targeting different cytokeratins can have the same fluorophore.

The endothelial markers can be used for enrichment as described above but could also be used for fluorescent labelling and the detected fluorescence can be used to calculate the classifier.

A further parameter may be fluorescence from one or more fluorescently labelled endothelial markers. An endothelial marker is a marker preferentially expressed in/on endothelial cells. Said endothelial marker is preferably not particularly expressed in or on any other cell type.

In a preferred embodiment, the fluorescence from the endothelial marker is used to single sort the fetal cells.

Such an endothelial marker can be selected from the group consisting of Thy-1 CD90, Thrombomodulin CD141, Human Endoglin CD105, Human Vimentin Vim, Vascular Cell Adhesion Molecule VCAM, Intercellular Adhesion Molecule 1 ICAM, Vascular Endothelial Growth Factor Receptor 1 (Flt-1) VEGFR-1, Vascular Endothelial Growth Factor Receptor 2 VEGFR-2, Vascular Endothelial Growth Factor Receptor 3 VEGFR-3, Plasminogen Activator Inhibitor 1 PAI-1, Endothelial Protein C Receptor EPCR, CD146, ITGA5, ITGB5, CDH11, CDH3 and CD59.

In preferred embodiments the endothelial marker is CD105 and/or CD141.

In another preferred embodiment, the endothelial marker is CD90, CD105 and CD141.

Fluorescent labelling agents against the endothelial marker is covalently conjugated as known for a person skilled in the art. In preferred embodiments with Alexa Fluor-488. In another preferred embodiment with FITC.

In one embodiment, a marker specific for maternal blood cells are used. A suitable marker for maternal cells will be markers not expressed on the fetal cells. A preferred maker is a leucocyte marker.

In preferred embodiments the maternal marker is a blood cell marker, such as CD14 and/or CD45.

In another preferred embodiment, the blood cell marker is the combination of markers against CD3, CD14, CD15, CD16, and CD19.

A particular feature of the invention is the specific labelling of cells using fluorescent labelling agents. These agents can be any type of molecule that is capable of binding specifically to a particular type of cell, e.g. through binding to a marker on the surface or inside the cells.

One preferred group of fluorescent labelling agents are antibodies.

A labelling agent may, according to the invention, be an antibody, such as any suitable antibody known in the art including other immunologically active fragments of antibodies or single chain antibodies. Antibody molecules are typically Y-shaped molecules whose basic unit consist of four polypeptides, two identical heavy chains and two identical light chains, which are covalently linked together by disulfide bonds. Each of these chains is folded in discrete domains. The C-terminal regions of both heavy and light chains are conserved in sequence and are called the constant regions, also known as C-domains. The N-terminal regions, also known as V-domains, are variable in sequence and are responsible for the antibody specificity. The antibody specifically recognizes and binds to an antigen mainly through six short complementarity-determining regions located in their V-domains.

The labelling agent may be a single moiety, e.g., a polypeptide or protein, or it may include two or more moieties, e.g., a pair of polypeptides such as a pair of single chain antibody domains. Methods of generating antibodies are well known to a person skilled in the art, by immunisation strategies for the generation of monoclonal or polyclonal antibodies or in vitro methods for generating alternative binding members. Polyclonal antibodies may be such as sheep, goat, rabbit or rat polyclonal antibody.

In addition any suitable molecule capable of high affinity binding may be used including antibody fragments such as single chain antibodies (scFv), particularly, Fab and scFv antibodies which may be obtained by phage-display (see below) or single domain antibodies (VHH) or chimeric antibodies. The labelling agent may be derived from a naturally occurring protein or polypeptide; it may be designed de novo, or it may be selected from a library. For example, the labelling agent may be derived from an antibody, a single chain antibody (scFv), a single domain antibody (VHH), a lipocalin, a single chain MHC molecule, an Anticalin™ (Pieris), an Affibody™, a nanobody (Ablynx) or a Trinectin™ (Phylos). Thus, methods of generating binding members of various types are well known in the art.

In one embodiment of the invention the labelling agent is a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab') 2 fragment that has two antigen binding fragments which are capable of cross-linking antigen, and a residual other fragment (which is termed pFc').

Additional fragments can include diabodies, linear antibodies, single-chain antibody molecules, and multispecific antibodies formed from antibody fragments.

In one preferred embodiment, the present invention relates to labelling agents derived from a naturally occurring protein or polypeptide; said protein or polypeptide may for example be designed de novo, or may be selected from a library. The labelling agent may be a single moiety, e.g., a polypeptide or protein domain, or it may include two or more moieties, e.g., a pair of polypeptides. The labelling agent may for example, but exclusively, be a lipocalin, a single chain WIC molecule, an Anticalin™ (Pieris), an Affibody™ (Affibody), or a Trinectin™ (Phylos), Nanobodies (Ablynx). The labelling agent may be selected or designed by recombinant methods known by people well known in the art.

In another embodiment of the invention the labelling agent is an affibody, such as any suitable affibody known in the art, in particular antibodies as defined herein, such as affibodies or immonologically fragments of affibodies. Affibodies are selected in vitro, from an affibody library constructed by combinatorial variation of the IgG binding domain of Protein A. Protein A is a surface protein from the bacterium *Staphylococcus aureus*. The binding domain consists of 58 residues, where of 13 are randomized to generate Affibody® libraries Thus, the size of an affibody is considerably less than of an antibody (www.affibody.com).

Finally, the labelling agent may be a receptor ligand directly or indirectly linked to a fluorophore.

Accordingly, it is an object of the present invention to provide for the selective labelling of fetal cells in the maternal biological sample based on a hybridisation technique. Alternatively, probes recognising mRNA selectively expressed by fetal cells may be used.

Fetal cell specific RNA, generally messenger RNA (mRNA) sequences may be used as fetal cell markers. The presence of such mRNA indicates that the gene for the fetal protein is being transcribed and expressed. The probes used to label fetal cells in a sample containing fetal and maternal cells include nucleic acid molecules, which comprise the nucleotide sequence complementary to the nucleotide sequence of the RNA molecule encoding a specific protein. Fetal cells contain distinct mRNAs or RNA species that do not occur in other cell types. The detection of these RNAs, can serve to label cells of fetal origin.

Likewise, maternal cells may be labelled using a probe specific for a maternal cell mRNA.

According to the invention the probe may be any type of probe known in the art for detection of RNA or DNA molecules. Conventional probes known by a person skilled in the art comprise, RNA and DNA probes synthesised from nucleotides of deoxynucleotide, respectively using a commercial synthesiser. Probes may be comprised of the natural nucleotide bases or known analogues of the natural nucleotide bases. It is further contemplated that the probes may be oligomers comprising one or more nucleotide analogs including peptide nucleic acids and other synthetic molecules capable of Watson Crick-base pairing.

For detection of chromosomal DNA, Fluorescence In Situ Hybridization (FISH) is frequently employed.

In one embodiment, a labelling agent (such as an antibody) or a synthetic probe is directly labelled, by having fluorophores covalently attached thereto. In another embodiment, a labelling agent (such as an antibody) or a synthetic probe is indirectly labelled, by being bound by a second agent having fluorophores covalently attached thereto. The binding of such probes or labelling agents to the target in the cell may be observed under a microscope as a bright fluorescence or may be detected by a FACS.

By use of a combination of labelling methods it is possible to enhance the signals from the fetal cells, thereby facilitating the identification thereof.

In order to enhance the probability and/or selectivity of identifying the fetal cells over the background of maternal cells, two or more selective labellings may be performed. The two or more labellings may be a combination of any of the labellings used for single labelling described above. Accordingly, the combined labelling may be carried out by the use of two or more different hybridisation probes, such as a combination of a DNA probe and a PNA or LNA probe for hybridisation with the same fetal RNA or more preferred with different fetal RNAs. Also, two or more different DNA probes (or PNA probes, or similar probes capable of specific hybridisation) may be used for hybridisation with different fetal RNAs. Likewise a combination of different labelling agents may be used, either with specificity for the same fetal antigen or with specificity for different antigens. In further embodiments labelling with a combination of nucleotide probes and labelling agents may be performed.

The fluorophore is selected to emit in the wave-length area of the detection means, and furthermore in suitable combination with an optional second labelling. In particular the fluorophores may be selected from FITC (fluorescein-isofluocyanate) or TRITC (Rhodanine Tetramethyl-isofluocyanate) having excitation at 495 nm and 520-530 nm, respectively. Further fluorophores which may be used are listed in the following tables with wavelength of excitation and emission of various flourochromes:

TABLE 1a

Reactive and conjugated probes

| Fluorochome | Ex (nm) | Em (nm) | MW | Notes |
|---|---|---|---|---|
| Hydroxycoumarin | 325 | 386 | 331 | Succinimidyl ester |
| Aminocoumarin | 350 | 445 | 330 | Succinimidyl ester |
| Methoxycoumarin | 360 | 410 | 317 | Succinimidyl ester |
| Cascade Blue | 375; 400 | 423 | 596 | Hydrazide |
| Lucifer yellow | 425 | 528 | | |
| NBD | 466 | 539 | 294 | NBD-X |
| R-Phycoerythrin (PE) | 480; 565 | 578 | 240 | |
| PE-Cy5 conjugates | 480; 565; 650 | 670 | | aka Cychrome, R670, Tri-Color, Quantum Red |
| PE-Cy7 conjugates | 480; 565; 743 | 767 | | |

TABLE 1a-continued

Reactive and conjugated probes

| Fluorochome | Ex (nm) | Em (nm) | MW | Notes |
|---|---|---|---|---|
| APC-Cy7 conjugates | 650; 755 | 767 | | PharRed |
| Red 613 | 480; 565 | 613 | | PE-Texas Red |
| Fluorescein | 495 | 519 | 389 | FITC; pH sensitive |
| FluorX | 494 | 520 | 587 | (AP Biotech) |
| BODIPY-FL | 503 | 512 | | |
| Tetramethylrhodamine | 550 | 560-608 | 444 | TRITC |
| Tetramethylrhodamine isothiocyanate | 547 | 530-560 | | |
| X-Rhodamine | 570 | 576 | 548 | XRITC |
| Lissamine Rhodamine B | 570 | 590 | | |
| PerCP | 490 | 675 | | Peridinin chlorphyll protein |
| Texas Red | 589 | (603) 615 | 625 | Sulfonyl chloride |
| Allophycocyanin (APC) | 650 | 660 | 104 | |
| TruRed | 490, 675 | 695 | | PerCP-Cy5.5 conjugate |

TABLE 1b

Alexa Fluor dyes (Molecular Probes)

| Fluorochome | Ex (nm) | Em (nm) | MW |
|---|---|---|---|
| Alexa Fluor 350 | 346 | 445 | 410 |
| Alexa Fluor 430 | 430 | 545 | 701 |
| Alexa Fluor 488 | 494 | 517 | 643 |
| Alexa Fluor 532 | 530 | 555 | 724 |
| Alexa Fluor 546 | 556 | 573 | 1079 |
| Alexa Fluor 555 | 556 | 573 | 1250 |
| Alexa Fluor 568 | 578 | 603 | 792 |
| Alexa Fluor 594 | 590 | 617 | 820 |
| Alexa Fluor 633 | 621 | 639 | 1200 |
| Alexa Fluor 647 | 650 | 668 | 1250 |
| Alexa Fluor 660 | 663 | 690 | 1100 |
| Alexa Fluor 680 | 679 | 702 | 1150 |
| Alexa Fluor 700 | 696 | 719 | |
| Alexa Fluor 750 | 752 | 779 | |

TABLE 1c

Spectrum dyes (Vysis)

| Fluorochome | Ex (nm) | Em (nm) |
|---|---|---|
| SpectrumOrange | 559 | 588 |
| SpectrumGreen1 | 497 | 524 |
| SpectrumGreen2 | 509 | 538 |
| SpectrumAqua | 433 | 480 |
| SpectrumBlue | 400 | 450 |
| SpectrumGold | 530 | 555 |
| SpectrumRed | 592 | 612 |
| SpectrumFRed (far red) | 655 | 675 |

TABLE 1d

Cy Dyes (AP Biotech)

| Fluorochome | Ex (nm) | Em (nm) | MW |
|---|---|---|---|
| Cy2 | 489 | 506 | 714 |
| Cy3 | (512); 550 | 570; (615) | 767 |
| Cy3.5 | 581 | 596; (640) | 1102 |
| Cy5 | (625); 650 | 670 | 792 |
| Cy5.5 | 675 | 694 | 1128 |
| Cy7 | 743 | 767 | 818 |

Unlabelled labelling agents may be used as known in the art, by use of a second labelling step with e.g. a secondary antibody against the unlabelled primary antibody, said antibody being labelled as discussed above, such as fluorophore labelled. By this two-step it may be possible to enhance the signals from the fetal cells. Further detection steps may be included by using indirect labelling as described here below.

Fluorescently labelled antibodies can be labelled directly or indirectly by at least one fluorophore. A person skilled in the art, will be able to select suitable fluorophores and can be any fluorophore such as Alexa Fluor 488, Alexa Fluor 555, Fluorescein isothiocyanate (FITC), Phycoerythrin (PE), BV421.

When more than one epithelial marker is used, these markers may be linked to the same fluorophore. This is because often there is no need to discriminate between cells having the different markers. The same applies to cases where more than one endothelial marker is used and/or where more than one maternal cell marker is used.

Indirect labelling of fluorescently labelled agents can be done by attaching a fluorophore to secondary antibodies binding the labelling agent bound to the markers.

In a preferred embodiment, the secondary antibody may be selected from FITC (fluorescein-isofluocyanate) or TRITC (Rhodanine Tetramethyl-isofluocyanate) having excitation at 495 nm and 520-530 nm, respectively. Further fluorophores which may be used are listed in the above table.

In another preferred embodiment, the secondary antibody may be selected from Alexa Fluor 488 or Alexa Fluor 555 having excitation at 490 nm and 555 nm, respectively.

As the flow cytometer will pick up smaller particles and quantify parameters for these as well, a marker for a eukaryotic cell is preferably used. For a person skilled in the art, such a dye will typically be a DNA-intercalating dye and can be dyes such as any Hoechst dye, DAPI, propidium iodide, 7-AAD, Vybrant DyeCycle Stains, SYTOX stains, or SYTO stains.

In another embodiment the dye is Vybrant DyeCycle Ruby Stain.

It is an object of the present invention to provide semi-automated or fully automated methods for isolation of single fetal cells by analysing cells sorted in a cell sorter using one or more measured parameters used to distinguish fetal cells from maternal cells and debris. The measured parameters can be used to calculate a fetal origin classifier. Thereby it is possible to identify single sorted cells that are fetal or that have a high likelihood of being fetal. The isolated cells can be used for genetic analysis of the fetal genotype.

One aspect of the invention relates to a method of isolating fetal cells from a biological sample of a pregnant woman, said method comprising the steps of a. providing a biological sample from said pregnant woman, the biological sample comprising a cellular fraction,
b. contacting cells comprised in said cellular fraction with one or more fluorescent labelling agents directed against at least one fetal cell epithelial marker and/or endothelial marker,
c. sorting said cells by Fluorescence-activated cell sorting (FACS) based on detection of said one or more fluorescent labelling agents bound to cells, and
d. identifying fetal cells among said sorted cells comprising a step of assigning a fetal origin classifier to individual sorted cells.

In one embodiment, wherein the cellular fraction is enriched for fetal cells prior to FACS.

The enrichment may comprise enriching for cells expressing at least one endothelial marker. Examples of endothelial markers are described further herein.

In a preferred embodiment, a fetal origin classifier is used to distinguish fetal cells from maternal cells. Ideally this is done with so high certainty, that there is no need of verifying fetal origin as described below.

In one embodiment, the fetal origin classifier is a binary classifier classifying the cell as fetal or non-fetal. Said fetal origin classifier may be calculated using artificial intelligence, neural network, random forest, machine learning, regression analysis, or classification trees using a training set comprising fetal and maternal cells of verified origin.

In some embodiments, the fetal origin classifier is binary, i.e. each cell is classified as being likely fetal or not likely fetal. In other embodiments, the classifier assigns a probability of fetal origin to each cell.

In some embodiments, the fetal origin classifier is calculated based on the verified origin of the fetal cell. Such as verifying the origin of fetal cells by obtaining a fetal genotype for individually sorted cells as described further below.

The fetal origin classifier is calculated based on the parameters detected in the FACS for each cell. Thus, the method assigns a particular fetal origin classifier to each sorted cell. After the cells from one maternal sample have been sorted, the end result may be a sorted array of cells with associated fetal origin classifier. The data is organised so that it is possible to associate each sorted cell with its particular fetal origin classifier.

In the next steps of genetic analysis of cells, one may start out with the cells having assigned the highest probability of being of fetal origin and if necessary one can continue with the next highest value etc. For an analysis of DNA in a fetal cell, only one cell from the fetus is required. In order to be more certain, it may be preferred to analyse more than one cell from a fetus, such as for example at least 3 cells from the same fetus.

The probability may be calculated with a function obtained from regression using a training set comprising fetal and maternal cells of verified origin.

In a preferred embodiment the regression analysis is logistic regression.

A person skilled in the art will know a logistic regression to be either the natural logarithm or the common logarithm. The logistic regression comprises a constant parameter and specific values for the parameters, obtained from the quantification of fluorescence, to calculate a probability.

In one embodiment, the biological sample is a blood sample, such as a peripheral blood sample.

The blood sample can have a volume of 5-30 ml. The samples can be obtained in any tube suitable for blood samples.

I another preferred embodiment, the blood sample can have a volume of 2-100 mL, such as 3-70, 5-50 mL, 5-30 mL and 10-30 mL.

In one embodiment, a cellular fraction is separated from the biological sample, suitably by centrifuging said biological sample. Centrifugation of the biological sample will preferably be between 0 and 25 minutes, more preferably between 0 and 15 minutes and most preferably between 5 and 10 minutes. The centrifugal force applied to the sample will preferably be between 0 and 5000 G, more preferably between 500 and 3000 G and most preferably between 1000 and 2000 G, such as 1600 G.

A person skilled in the art will know the centrifugation to separate a blood sample into a plasma- and cellular fraction.

The cellular fraction will comprise of red blood cells, white blood cells (leucocytes) and fetal trophoblasts, fetal extravillous trophoblasts, and fetal endovascular trophoblasts.

In another embodiment, the biological sample is a cervical smear. Mucus from the swab may first be dissolved using acetic acid or DDT. The cellular fraction achieved after this step may then be fixed in paraformaldehyde. The cellular fraction from the cervical smear comprises fetal cells (trophoblasts, such as cytotrophoblasts, syncytiotrophoblast and/or interstitial trophoblasts) and squamous epithelial cells, columnar epithelial cells, white blood cells and red blood cells. Following that the fetal cells may be enriched using HLA-G and or CD105/CD141 and stained as herein described for blood samples In one embodiment of the invention, fixation of the cells of a maternal sample greatly increases stability of fetal cells in a maternal sample, while allowing enrichment and identification of fetal cells e.g. as further described herein above. In one embodiment the fixation procedure can be performed on a non-enriched sample immediately after sampling (i.e. step a of the method described in the first embodiment), resulting in fixation of cellular components in the maternal sample. At the same time the fixation is so mild that maternal erythrocytes can be lysed selectively in a subsequent lysis step.

Fixation is preferably done for between 1 and 60 minutes. More preferably fixation is done for between 5 and 30 minutes and most preferably, fixation is done between 5 and 15 minutes such as 10 minutes.

The fixation solution preferably comprises between 0.5% and 7.5% paraformaldehyde, more preferably 1% and 6% and most preferably between 1.5% and 2%.

In addition to paraformaldehyde, the fixation solution preferably comprises salt at a concentration between 0.05 M and 0.3 M. More preferably the salt concentration is between 0.1 M and 0.2 M and most preferred is a concentration between 0.125 M and 0.175 M.

Preferably, the fixation step may be followed by a step of lysis of red blood cells comprising contacting the fixated sample of step a with a lysis buffer The lysis buffer typically comprises a non-ionic detergent, preferably Triton-X-100. Preferred concentrations of the detergent are between 0.01% (w/w) and 0.5%, more preferably between 0.05%-0.3%, and most preferably 0.1%.

In a preferred embodiment, the lysis step is performed immediately after the fixation step. That is both the fixation and the lysis is performed after step a and before step b of the method described in the first embodiment. I.e. the lysis solution is added directly to the sample, e.g. after fixation for 10 minutes. Lysis is typically done for a period of 1 minutes to 120 minutes, more preferably 5 to 60 minutes and most preferably for 6 to 10 minutes.

The lysis buffer can, in addition to lysis of red blood cells, also create small openings in the cell membranes of the white blood cells which allows the labelling agents to penetrate the cell membrane and bind to their target antigens.

The origin of fetal cells is verified by obtaining a fetal genotype for individually sorted cells. When the genotype is distinct from the maternal genotype, the cell will be of fetal origin. Such a verification can be done by short tandem repeat analysis (STR analysis).

In another embodiment the verification can be done by first amplifying the genome and subjecting some of the material to a short tandem repeat analysis (STR analysis).

In another embodiment the verification is done by analysing single nucleotide polymorphisms (SNP's) i.e. on a SNP array, after a whole genome amplification.

In a further embodiment, the fetal origin is verified by any of the methods suitable for detecting genetic markers, as described further below. Such as for example Next Generation Sequencing (NGS).

In a second aspect, the invention relates to a method of determining a genetic abnormality in a fetus said method comprising the steps of
a. Obtaining one or more fetal cells isolated by a method as defined herein, and
b. Detecting one or more genetic markers associated with said genetic abnormality in the genome of said fetal cell The genetic markers are detected using one or more methods selected from the group consisting of RFLP, southern blot analysis, Microarray-based Comparative Genomic Hybridization (aCGH), Short Tandem Repeat analysis (STR analysis), whole genome amplification, whole genome scan, SNP array, Polony sequencing, Shotgun sequencing, Massively Parallel Signature Sequencing (MPSS), Sanger Sequencing, PCR-based methods and Next-Generation Sequencing methods.

The Next-Generation Sequencing methods can be selected from the group consisting of Illumina (Solexa) sequencing, Roche 454 sequencing, Ion torrent: Proton/PGM sequencing and/or SOLiD sequencing.

The genetic abnormality is aneuploidy, monosomy, polysomy, trisomy, copy number variation (CNV), single nucleotide variation (SNV), or a monogenic disorder.

In some embodiments, the DNA content from a single fetal cell has to be amplified to be able to perform methods to detect and verify genetic markers.

Several methods have been developed for high-fidelity whole genome amplification, including Multiple Displacement Amplification (MDA), Degenerate Oligonucleotide PCR (DOP-PCR) and Primer Extension Preamplification (PEP). While DOP-PCR and PEP are based on standard PCR techniques, MDA can be achieved with an isothermal reaction setup.

The detection/analysis of fetal DNA can be performed by the following methods: SNP genotyping with TaqMan primer/probe sets, qPCR- and PCR-based mutation detection, Next-generation sequencing (NGS), Short Tandem Repeats/microsatellite analysis, Sanger sequencing, RFLP and Southern blot analysis and Array technologies, such as comparative genomic hybridization.

Fetal conditions that can be determined based on the methods and systems herein include the presence of a fetus and/or a condition of the fetus such as fetal aneuploidy. Such a fetal abnormality can e.g be trisomy 13, trisomy 18, trisomy 21 (Down Syndrome), Klinefelter Syndrome (XXY) and other irregular number of sex or autosomal chromosomes.

Other fetal conditions that can be detected using the methods herein include segmental aneuploidy, such as Ip36 duplication, dup(17)(p11.2p11.2) syndrome, Down syndrome, Pelizaeus-Merzbacher disease, dup(22)(q11.2q11.2) syndrome, Cat eye syndrome.

In one embodiment, the fetal abnormality to be detected is due to one or more deletions in sex or autosomal chromosomes. These abnormalities include Cri-du-chat syndrome, Wolf-Hirschhorn syndrome, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, steroid sulfatase deficiency, Kallmann syndrome, Microphthalmia with linear skin defects, Adrenal hypoplasia, Glycerol kinase deficiency, Pelizaeus-Merzbacher disease, testis-determrning factor on Y, Azospermia (factor a), Azospermia (factor b), Azospermia (factor c) or Ip36 deletion.

In some cases, the fetal abnormality is an abnormal decrease or increase in chromosomal number, such as XO syndrome.

EXAMPLES

The antibodies mentioned in the example section are the specific antibodies mentioned in the following table:

TABLE 2

Antibodies used in examples. Antibodies denoted with FITC or PE are directly conjugated antibodies.

| Antibody | Company | Catalog number |
| --- | --- | --- |
| CK7 | Abcam | ab181598 |
| CK8 | Abcam | ab53280 |
| CK18 | Abcam | ab32118 |
| CK19 | Abcam | ab52625 |
| CK wide spectrum | Abcam | ab9377 |
| CD105-FITC | Miltenyi Biotec | 130-098-774 |
| CD141-FITC | Miltenyi Biotec | 130-090-513 |
| CD90-FITC | Miltenyi Biotec | 130-114-859 |
| CD3-PE | Thermo Fischer Scientific | 12-0038-42 |
| CD14 | BD Biosciences | 551403 |
| CD14-PE | Thermo Fischer Scientific | 12-0149-42 |
| CD15-PE | Thermo Fischer Scientific | 12-0159-42 |
| CD16-PE | Thermo Fischer Scientific | 12-0168-42 |
| CD19-PE | Thermo Fischer Scientific | 12-0199-42 |
| CD45 | Thermo Fischer Scientific | MA5-17687 |
| Goat anti-rabbit Alexa Fluor 488 | Thermo Fischer Scientific | LifeA11070 |
| Goat anti-rat Alexa Fluor 555 | Thermo Fischer Scientific | LifeA21434 |

Example 1—Enrichment and Staining of Fetal Cell Using MACS, Followed by Second Enrichment of Fetal Cells Using FACS, Followed by Scanning and Picking of Fetal Cells Using CellCelector Blood samples were collected from 13 pregnant women between the gestational ages of 10 to 14 weeks. Samples were processed and fetal cells enriched using the following methods:

Blood Processing

A total of 30 mL of peripheral blood was collected in Cell-Free DNA BCT® Tubes (Streck, Omaha, USA). The blood samples were centrifuged at 1000-2000 g for 2-10 minutes and plasma was removed. The blood samples were fixed in a 1-10% formaldehyde buffer in phosphate-buffered saline (PBS) for 2-10 minutes, followed by lysis of red blood cells in 0.1-1% Triton-X-100 detergent in PBS for 6-10 minutes. The cells were subsequently washed in PBS and a 0.5% bovine serum albumin buffer and pelleted before fetal cell enrichment.

Fetal Cell Enrichment and Staining Using Miltenyi's Magnetic Activated Cell Sorting (MACS)

Fetal cell enrichment was performed using MACS, (Miltenyi Biotec, Germany). The pelleted unenriched cells after 'blood processing' were incubated with CD105 and CD141 antibodies (microbeads) for 15 minutes to 1 hour, and the cell suspension was applied to MACS columns for enrichment. The retained cells were plunged in a 15 mL tube and washed (centrifugation for 10 minutes), before reapplying the enriched cells to a second column for antibody staining. The staining was performed on the column by incubating the enriched cell fraction with a cocktail of primary cytokeratin antibodies that target fetal cells, and CD14 and CD45 antibodies that target maternal white blood cells, for 15 minutes to 1 hour. After incubation with the primary antibodies, the cells in the columns were rinsed thrice with PBS. Following that, secondary antibodies labelled with the following fluorescent dyes: Alexa Fluor 488 (AF488) (targeting CKs on the fetal cells) and Alexa Fluor 555 (AF555) (targeting CD14 and CD45 on maternal white blood cells) were applied, and the cells incubated for 15 minutes to 1 hour. The stained cells were washed twice in PBS before being plunged and saved at 4° C. until FACS.

Figure 2:
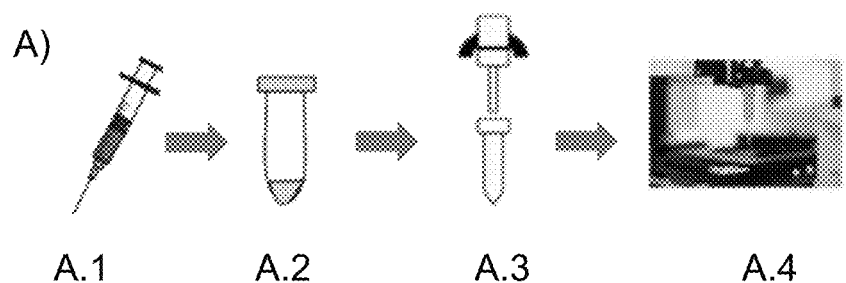
Figure 2:
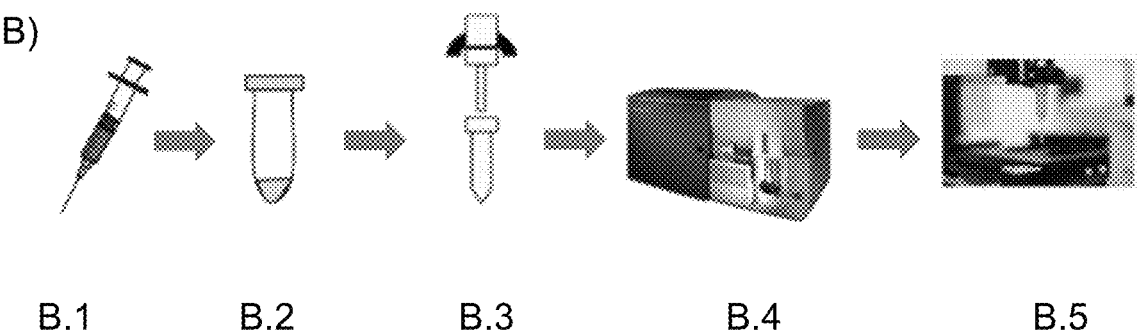
Figure 3:
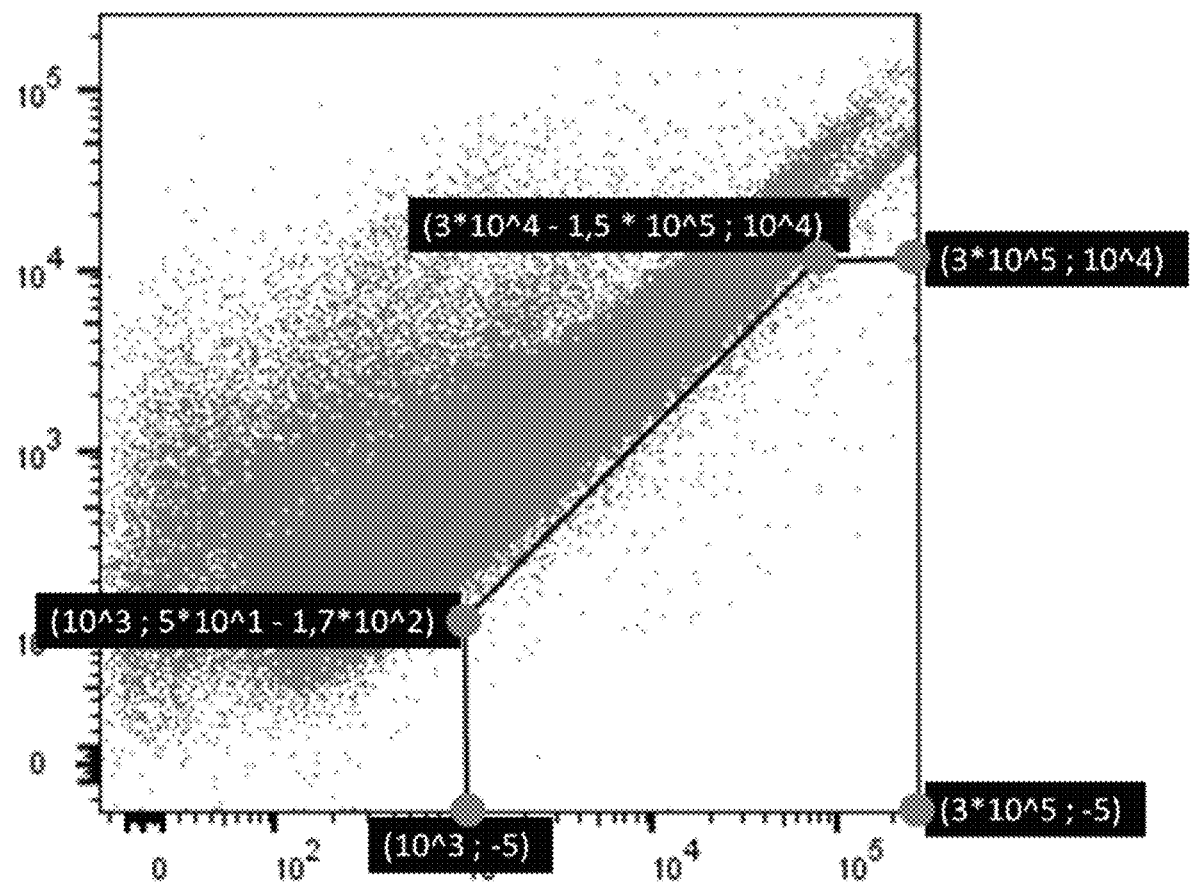

Fetal Cell Enrichment Using FACS 20 uL 5 uM Hoechst 33342 was added to the MACS enriched cells. The cells were run through a FACS instrument for another step of enrichment (FIG. 2). Fetal cells were sorted on a FACS Aria III (BD Biosciences, USA), with 405 nm (Hoechst 33342), 488 nm (Alexa Flour 488) and 561 nm (Alexa Fluor 555) lasers. Fluorescence signals were collected with the respective bandpass filters: 450/50 nm, 530/30 nm and 585/42 nm. No fluorescence compensation or doublet exclusion was made. The photomultiplier tube voltage was set on the following parameters: FSC 300, SSC 390, AF488 360, AF555 236, Hoechst 500, and FSC-H threshold was 5000. A 100 μm nozzle was applied, and the FACS instrument was set to sort in yield mode due to the rarity of circulating fetal cells. All cells were included in the forward-scatter/side-scatter (FSC/SSC) plot. From the Hoechst fraction, an area (gate G1) was made in the AF488/AF555 fluorescence plot to sort the cells of interest. Analysis of sorted cells was performed using FlowJo software (FlowJo, LLC USA). An example of the gate G1 with X-Y coordinates is shown in FIG. 3. On average 2244 cells were sorted. Cells were smeared on glass slides and classified using CellCelector (fluorescence scanner-cell-picker). There were 107 fetal cells among the sorted cells with an average of 7.9 fetal cells per sample (Table 3).

TABLE 3

Blood samples from thirteen pregnant women were processed as described in the text, and fetal cells further enriched using FACS. On average 342.000 events per sample where registered on the FACS and 7.9 fetal cells per sample were isolated.

| Sample no | Study | Gate | Sort precision | Total no. of events | No. of sorted cells | Fetal cells identified |
|---|---|---|---|---|---|---|
| HR725 | FACS: CD14-CD45_Gate1 | G1 | Yield | 171.739 | 1,567 | 4 |
| AALb149 | FACS: CD14-CD45_Gate1 | G1 | Yield | 327.956 | 664 | 3 |
| HR726 | FACS: CD14-CD45_Gate1 | G1 | Yield | 201.719 | 355 | 5 |
| HR729 | FACS: CD14-CD45_Gate1 | G1 | Yield | 394.992 | 1,770 | 2 |
| HR730 | FACS: CD14-CD45_Gate1 | G1 | Yield | 514.347 | 3,480 | 16 |
| HR731 | FACS: CD14-CD45_Gate1 | G1 | Yield | 694.326 | 2,723 | 14 |
| HR732 | FACS: CD14-CD45_Gate1 | G1 | Yield | 277.761 | 1,405 | 10 |
| HR733 | FACS: CD14-CD45_Gate1 | G1 | Yield | 283.559 | 2,192 | 16 |
| HE80 | FACS: CD14-CD45_Gate1 | G1 | Yield | n/a | 2,030 | 2 |
| HR734/MD23 | FACS: CD14-CD45_Gate1 | G1 | Yield | 352.250 | 5,831 | 2 |
| HR735 | FACS: CD14-CD45_Gate1 | G1 | Yield | 271.748 | 916 | 3 |
| HR736 | FACS: CD14-CD45_Gate1 | G1 | Yield | 313.574 | 4,731 | 25 |
| AAL163 | FACS: CD14-CD45_Gate1 | G1 | Yield | 301.522 | 1,503 | 1 |

Figure 4:
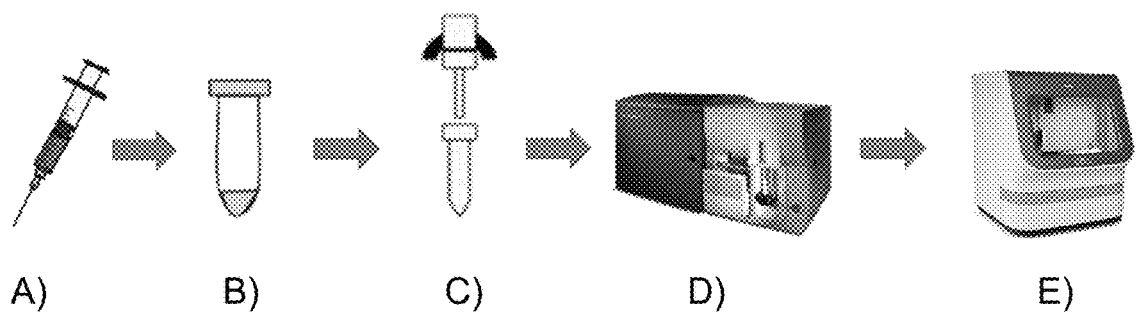
Figure 5:
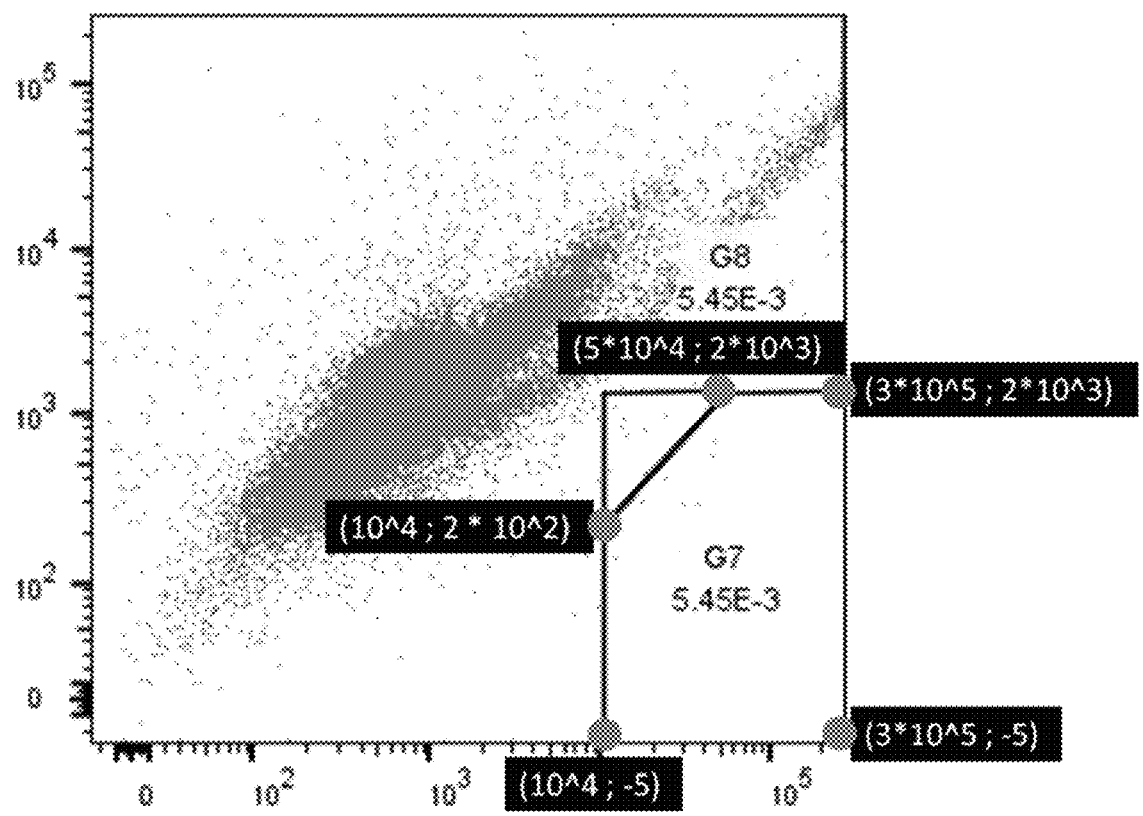
Figure 6:
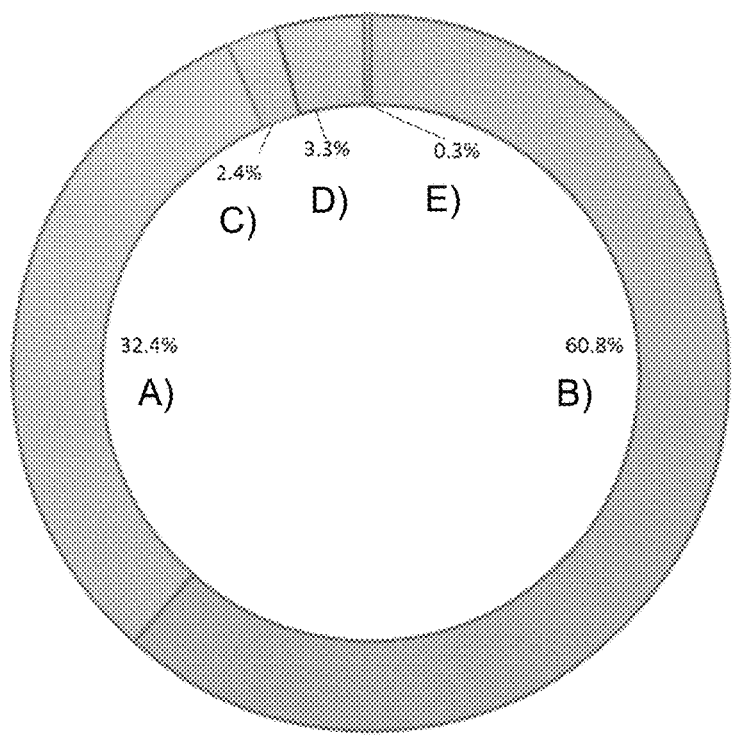

Example 2—Enrichment and Staining of Fetal Cell Using MACS, Followed by Single Cell Sorting of Fetal Cells Using FACS Blood samples of 30 mL were collected from 13 pregnant women between the gestational ages of 10 to 14. Samples were processed and fetal cells enriched on magnetic beads, stained using above methods and run through the FACS Aria III instrument with the settings as described in example 1. A sorting gate (G7) on the FACS graph for Alexa Fluor 488 and Alexa Fluor 555 (PE) was used to individually collect all the cells in that gate in single PCR tubes containing 5 μl TE buffer with an event rate of app. 100-600 events per second (FIG. 5). The sorted cells were frozen at −80° C. Using this gate, on average, 17 cells were collected from every sample. The cells were then subjected to short tandem repeat (STR) analysis to decipher their origin (fetal or maternal) (FIG. 4). Prior to STR analysis, fetal cells were lysed using PrepGem Universal (Zygem, New Zealand) according to manufacturer's instructions. A STR genotype profile was generated with fragment size capillary electrophoresis using an ABI 3500 Genetic Analyzer. Data analysis was performed in GeneMapper ID-X fragment size analyze software (Thermo Fischer Scientific, USA). The results from the STR analysis on single sorted cells is presented in Table 4 and FIG. 6.

TABLE 4

Data from single cell sorted samples. The origins (fetal or maternal) of the cells were deciphered by STR analysis. 13 consecutive samples were enriched with CD105 and CD141 microbeads using MACS, and subsequently single cell sorted on a FACS Aria III using cytokeratin, CD45, CD14 and Hoechst staining. Between 4 and 47 cells were sorted, and STR analysis revealed 3 to 36 fetal cells among the sorted cells with an average of 9.6 fetal cells per sample.

| Sample | Sorted cells/gate | Fetal cells | Maternal cells | No STR signals (empty tubes) cell contamination | Fetal cells with maternal contamination | Fetal cells with unknown |
|---|---|---|---|---|---|---|
| 2703 | 33 | 5 | 25 | 1 | 1 | 0 |
| 2711 | 4 | 3 | 0 | 1 | 0 | 0 |
| 2712 | 7 | 3 | 3 | 0 | 1 | 0 |
| 2726 | 47 | 34 | 7 | 2 | 2 | 2 |
| 2727 | 17 | 8 | 9 | 0 | 0 | 0 |
| 2733 | 6 | 3 | 3 | 0 | 0 | 0 |
| 2734 | 25 | 12 | 12 | 1 | 0 | 0 |
| 2741 | 9 | 8 | 1 | 0 | 0 | 0 |
| 2742 | 4 | 4 | 0 | 0 | 0 | 0 |
| 2748 | 20 | 10 | 10 | 0 | 0 | 0 |
| 2749 | 31 | 11 | 18 | 2 | 0 | 0 |

TABLE 4-continued

Data from single cell sorted samples. The origins (fetal or maternal) of the cells were deciphered by STR analysis. 13 consecutive samples were enriched with CD105 and CD141 microbeads using MACS, and subsequently single cell sorted on a FACS Aria III using cytokeratin, CD45, CD14 and Hoechst staining. Between 4 and 47 cells were sorted, and STR analysis revealed 3 to 36 fetal cells among the sorted cells with an average of 9.6 fetal cells per sample.

| Sample | Sorted cells/ gate | Fetal cells | Maternal cells | No STR signals (empty tubes) cell contam- ination | Fetal cells with maternal contam- ination | Fetal cells with unknown |
|---|---|---|---|---|---|---|
| HR752 | 10 | 8 | 0 | 0 | 1 | 0 |
| 2754 | 14 | 12 | 2 | 0 | 0 | 0 |

From 13 consecutive samples, 4-47 cells were sorted with an average of 17.5 cells (Table 4). Between 3 and 36 fetal cells were identified by STR analysis, giving an average of 9.6 fetal cells. Comparing with example 1 (7.9 fetal cells identified) this shows that single cell isolation is possible when sorting a MACS enriched sample on a FACS.

At this point, the origin (fetal or maternal) of all the single sorted cells was known. Also, for every cell, the recorded value for 5 different parameters (Forward scatter (FSC-A), Side scatter (SSC-A), Hoechst Blue-A (nuclei stain), Alexa Fluor 488-A (targeting CK antibodies on fetal cells), and Alexa Fluor 555 (PE-A) (targeting CD14 and CD45 on maternal white blood cells) on the FACS instrument was known. Given all this information, we developed a model, using a mathematical method called logistic regression, to predict the probability of localizing fetal cells for future samples where the STR information will not be available.

Model:

The model for predicting fetal cells is based on a mathematical method called logistic regression, which for every sample will give a probability of a single sorted cell being fetal or not.

The logistic function is as follows:

$$p(X) = \frac{e^{\beta_0 + \beta_1 X_1 + \ldots + \beta_p X_p}}{1 + e^{\beta_0 + \beta_1 X_1 + \ldots + \beta_p X_p}}$$

Where X1, X2 . . . Xp are specific variables measured for each single sorted cell. As mentioned, in our case we have five variables (FSC-A, SSC-A, Hoechst Blue-A, Alexa Fluor 488-A, and PE-A) measured by the FACS instrument. X1, X2, X3, X4, and X5 correspond to the values registered for FSC-A, SSC-A, Hoechst Blue-A, Alexa Fluor 488-A, and Alexa Fluor 555 (PE-A) for every cell, respectively.

$\beta_0$, $\beta_1$, $\beta_2$ . . . $\beta_p$ are the coefficients or constant values in the equation. In our case there are six coefficients where $\beta_0$ stands alone (reflects the probability when all the five variables are zero), $\beta_1$, $\beta_2$, $\beta_3$, $\beta_4$, and $\beta_5$ reflect the influence of FSC-A, SSC-A, Hoechst Blue-A, Alexa Fluor 488-A, and Alexa Fluor 555 (PE-A) respectively on the probability of a cell being fetal or maternal. However, this influence is not reflected by their absolute values. The six coefficients are constant values which are calculated from the 'training' dataset where the origin of the cells (fetal or maternal) and the value for all the five variables for each cell is known (in the current dataset it consists of 121 fetal cells and 90 maternal cells). These β values are calculated so that for all the cells in the 'training' dataset the fetal cells get as high a probability as possible (close to 1) and the maternal cells get as low a probability as possible (close to 0). These β values ($\beta_0$, $\beta_1$, $\beta_2$, $\beta_3$, $\beta_4$ and $\beta_5$) shown in Table 5 are unique to our data.

TABLE 5

Coefficients calculated from the dataset of 121 fetal cells and 90 maternal cells for which the values for the different variables from the FACS instrument were known.

| Coefficients | Values |
|---|---|
| β0 | 0,9064212 |
| β1 | 0,0000254 |
| β2 | −0,0000064 |
| β3 | 0,0000325 |
| β4 | −0,0000171 |
| β5 | −0,0032858 |

Running this algorithm for every single sorted cell in a sample, p(X) will give a value between 0 and 1. Higher the value of p(X) is for a given cell, higher does the algorithm estimate the probability that the cell is a fetal cell. We ran this model on three single cell sorted samples to test if we can enrich the number of fetal cells by focusing only on the 50% of the cells with highest probability of being fetal. The amount of fetal cells differed from 38-83% after sorting and focusing on the cells with highest probability this increased significantly. The results are shown in Table 6.

TABLE 6

Data from three single cell sorted samples, where the model of predicting fetal cells using logistic regression was tested. In all the three samples, the number of fetal cells was increased in the first half of the sample that was shown to have a high probability of being a fetal cell. This would facilitate throughput and also decrease COGS for downstream genetic analysis on single fetal cells.

| Sample | Total Cells Sorted | Confirmed Fetal Cells (by STR) | Confirmed maternal cells (by STR) | % of Fetal Cells in total population | % of Fetal Cells in top half probable fetal (using algorithm) |
|---|---|---|---|---|---|
| 2726 | 41 | 34 | 7 | 83% | 95% |
| 2749 | 29 | 11 | 18 | 38% | 78.5% |
| 2734 | 24 | 12 | 12 | 50% | 58.4% |

Figure 7:
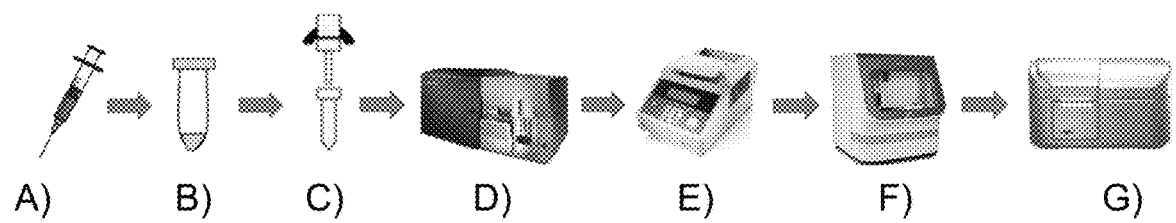

Implementing the model to predict the localization of fetal cells on the different FACS plots using the above approach is achieved, the workflow looks as in FIG. 7. After single sorting the cells, the DNA in all the cells will be amplified using whole genome amplification (WGA). A fraction of the WGA product would then be used to perform STR analysis. The rest of the DNA from the cells that turn out to be fetal would then be used for genetic analysis using aCGH or any other relevant downstream approach.

Example 3—Enrichment of Fetal Cells Using FACS, Followed by Scanning and Picking of Fetal Cells Using CellCelector In order to explore the possibility of FACS isolation of fetal cells without the need of enriching fetal cells using MACS enrichment, 10 mL of blood samples were collected from eight pregnant women in the gestational ages of 10 to 14 weeks. Blood samples were processed and white blood cells pelleted as described in example 1. After blood processing the cells were stained with a varying concentration of a cocktail of only CK antibodies in 4 samples and a cocktail of CK antibodies, plus CD14 and CD45 antibodies in 4 samples. Cells lying in gate G1 on the FACS plot for Alexa-Fluor 488 and Alexa Fluor 555 (PE) were sorted as in example 1. On average 55 mill. events where registered and 22,140 cells were sorted from every sample. Cells were smeared on glass slides and classified using CellCelector (fluorescence scanner-cell-picker). On average 4 fetal cells from 10 mL of whole blood were retrieved, showing that enrichment can be done exclusively using FACS (Table 7).

TABLE 7

Data from 8 samples where 10 mL of blood was processed, and cells were run through a FACS instrument without prior fetal cell enrichment

| Sample | Gate | Sort precision | Total events | Sorted cells/ gate | Total FC in sample | CK antibodies (µL) | CD14 + CD45 antibodies (µL) |
|---|---|---|---|---|---|---|---|
| 2537-WB | WB-G1 | yield | 60 mio | 14,642 | 4 | 5 | — |
| 2571-WB | WB-G1 | yield | 36 mio | 13,120 | 3 | 5 | — |
| 2580-WB | WB-G1 | yield | 60 mio | 41,454 | 4 | 5 | — |
| 2581-WB | WB-G1 | yield | 55 mio | 27.141 | 6 | 5 | — |
| 2591-WB | WB-G1 | yield | 51 mio | 20,288 | 9 | 3 | 3 |
| 2592-WB | WB-G1 | yield | 55 mio | 34,184 | 4 | 3 | 3 |
| 2637-WB | WB-G1 | yield | 60 mio | 17,755 | 2 | 3 | 3 |
| 2693-WB | WB-G1 | yield | 66 mio | 8,535 | 0 | 3 | 3 |

Example 4—Enrichment and Staining of Fetal Cell Using MACS, Followed by Single Cell Sorting of Fetal Cells Using FACS In order to explore the applicability of the invention on several FACS machines, we conducted the examples as shown in example 2 on a FACS Melody (BD Biosciences, USA) instead of a FACS Aria III. In the following example we show that fetal cells can be identified from 30 mL of blood which has been blood processed, enriched using antibodies specific for endothelial markers (CD105 and CD141) on a MACS platform, and subsequently stained for epithelial markers (CKs) as described in example 1. The enriched and stained cells were single cell sorted on a FACS Melody (BD Biosciences, USA) using cytokeratin, CD45, CD14 and Hoechst staining.

Single Cell Sorting Using FACS

Just before FACS, 20 µL of a 5 µM Hoechst 33342 solution was added to the enriched cell pellet to stain the nuclei.

The enriched and stained cells were sorted on a FACS Melody (BD Biosciences, USA) with a 405 nm, a 488 nm, and a 561 nm laser. Fluorescence signals were collected with the respective bandpass filters: 448/45 nm (Hoechst 33342), 527/32 nm (AF488) and 585/40 nm (AF555). No fluorescence compensation or doublet exclusion was made. The photomultiplier tube voltage was set on the following parameters: FSC: 278, SSC: 530, AF488: 336, AF555: 271, Hoechst: 470 and FSC threshold: 2939. A 100 µm nozzle was applied, and the FACS instrument was set to sort in yield mode due to the rarity of circulating fetal cells.

Figure 8:
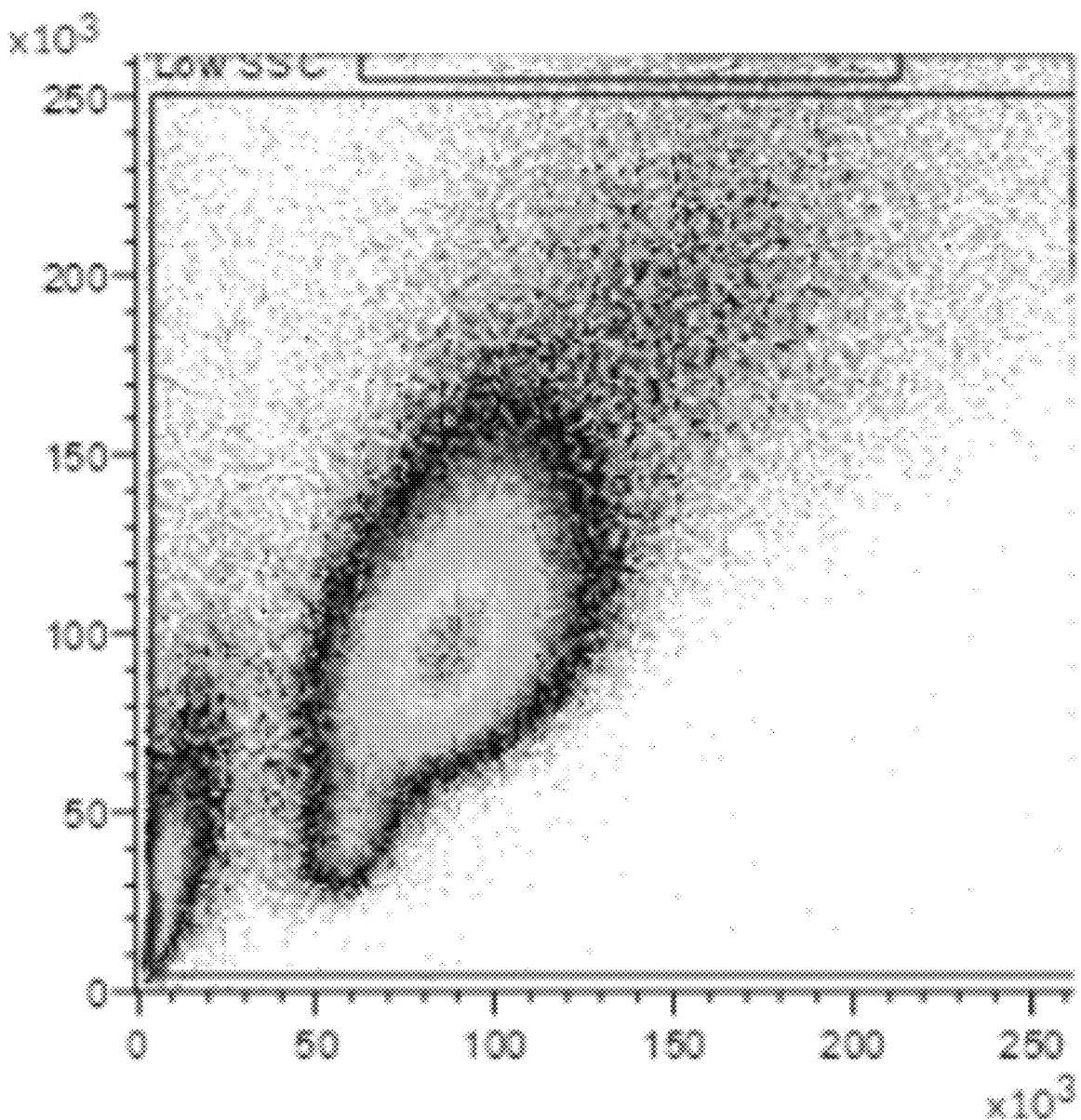

First, all events (debris) with very high side scatter (SSC) were excluded, and the remaining cells were gated for Hoechst$^+$ events. Subsequently, Hoechst$^+$ events were gated for being CK$^+$ and CD45$^-$ and CD14$^-$. An example of the gating strategy is shown in FIG. 8. Cells were sorted individually in 200 µl PCR tubes containing 5 µl TE buffer with an event rate of app. 100-600 events per second. The sorted cells were frozen at −80° C. The cells were then subjected to short tandem repeat (STR) analysis to decipher their origin (fetal or maternal) as described in example 2.

Experimental Results of Example 4

As seen in Table 8, between 10 and 26 cells were sorted with an average of 17.9 in 9 consecutive samples. By STR analysis, between 0 and 16 fetal cells were identified per sample with an average of 7.0 fetal cells. Comparing with example 1 (7.9 fetal cells identified) and example 2 (9.6 fetal cells isolated), showing that the choice of FACS machine does not have an effect on the result of the invention.

TABLE 8

9 consecutive samples were enriched with CD105 and CD141 microbeads using MACS, and subsequently single cell sorted on a FACS Melody using cytokeratin, CD45, CD14 and Hoechst staining. Between 10 and 26 cells were sorted, and STR analysis revealed 0 to 16 fetal cells among the sorted cells with an average of 7.0.

| Sample ID | Sorted cells | Fetal cells |
|---|---|---|
| HR843 | 20 | 11 |
| HR847 | 13 | 7 |
| 3057 | 12 | 6 |
| HR850 | 26 | 16 |

TABLE 8-continued 9 consecutive samples were enriched with CD105 and CD141 microbeads using MACS, and subsequently single cell sorted on a FACS Melody using cytokeratin, CD45, CD14 and Hoechst staining. Between 10 and 26 cells were sorted, and STR analysis revealed 0 to 16 fetal cells among the sorted cells with an average of 7.0.

| Sample ID | Sorted cells | Fetal cells |
|---|---|---|
| HR851 | 22 | 11 |
| HR854 | 22 | 8 |
| HR855 | 10 | 2 |
| HR856 | 14 | 0 |
| HR857 | 22 | 2 |

Example 5—Enrichment of Fetal Cell Using FACS, Followed by Single Cell Sorting of Fetal Cells Using FACS In order to explore if enrichment using MACS could be avoided, we replaced the MACS enrichment with a FACS enrichment, which was followed by single cell sorting on a FACS instrument. In other words, the cells were going through "double FACS". The FACS enrichment removed the majority of maternal cells and debris, which allowed subsequent single cell sorting of the fetal cells without maternal contamination. Identification of fetal cells in both rounds of FACS was solely based on cytokeratin, CD45, CD14 and Hoechst staining and no endothelial markers.

We collected 10 ml blood samples from 10 pregnant women in gestational ages of 10-14 weeks. Blood processing was performed as described in example 1.

Fetal Cell Staining

After blood processing, the cells pelleted in a tube were stained with primary antibodies targeting CK7, CK8, CK18, CK19, CK wide spectrum, CD14, and CD45 for 15 minutes to 1 h. The cells were then washed in PBS, centrifuged at 550 g for 10 minutes, and the supernatant was removed. Next, secondary antibodies labelled with AF488 (targeting CKs) and AF555 (targeting CD45+CD14) were added and incubated for 15 minutes to 1 h. The cells were washed twice, and the supernatant was removed to 500 µl.

FACS Enrichment and Single Cell Sorting

Just before sorting on a FACS Melody, the cells were stained with 500 µL of a 20 Hoechst 33342 solution, and PBS was added to make a final volume of 4 mL. The FACS settings were identical to the ones mentioned in Example 4.

Figure 9:
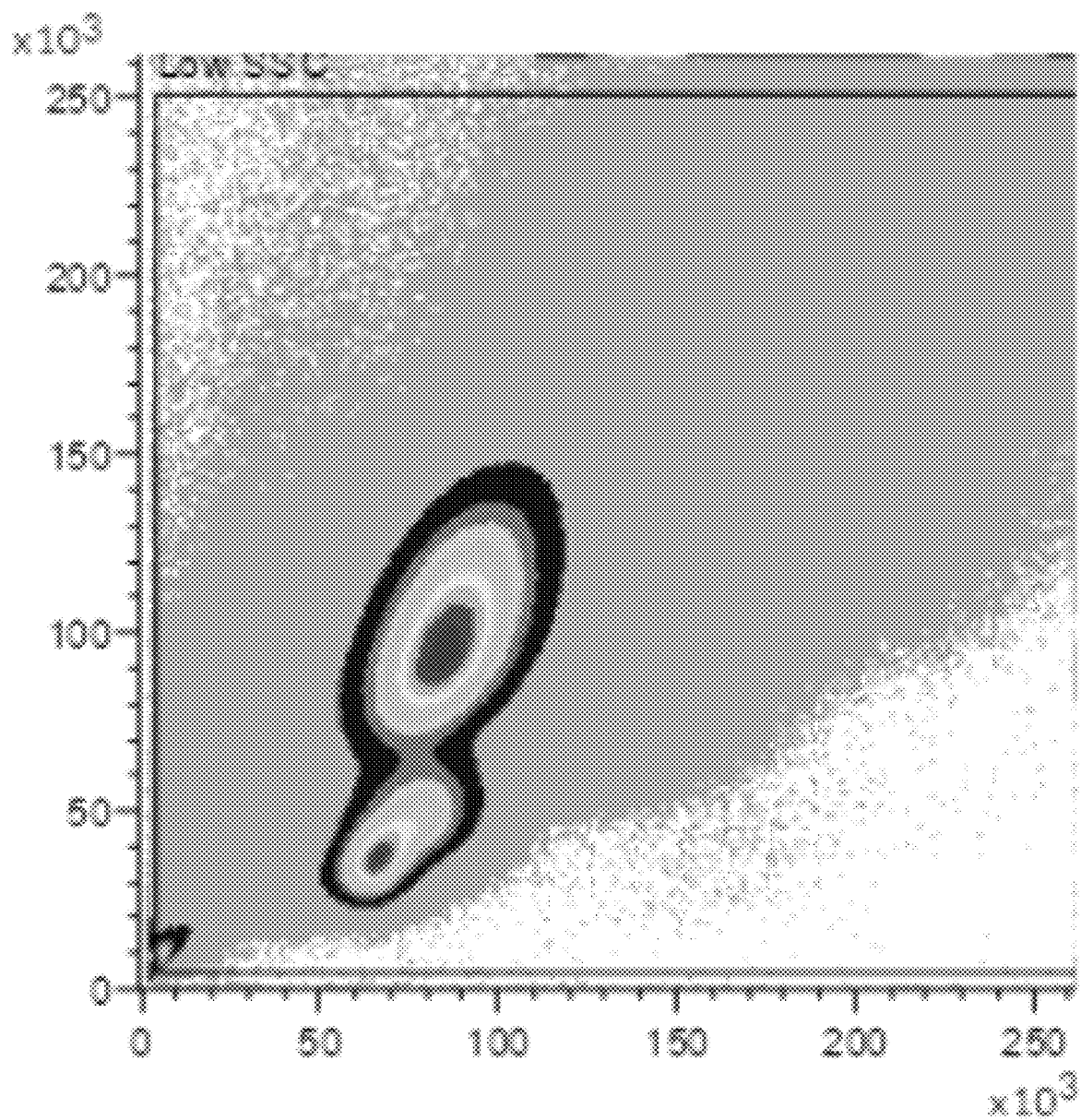
Figure 10:
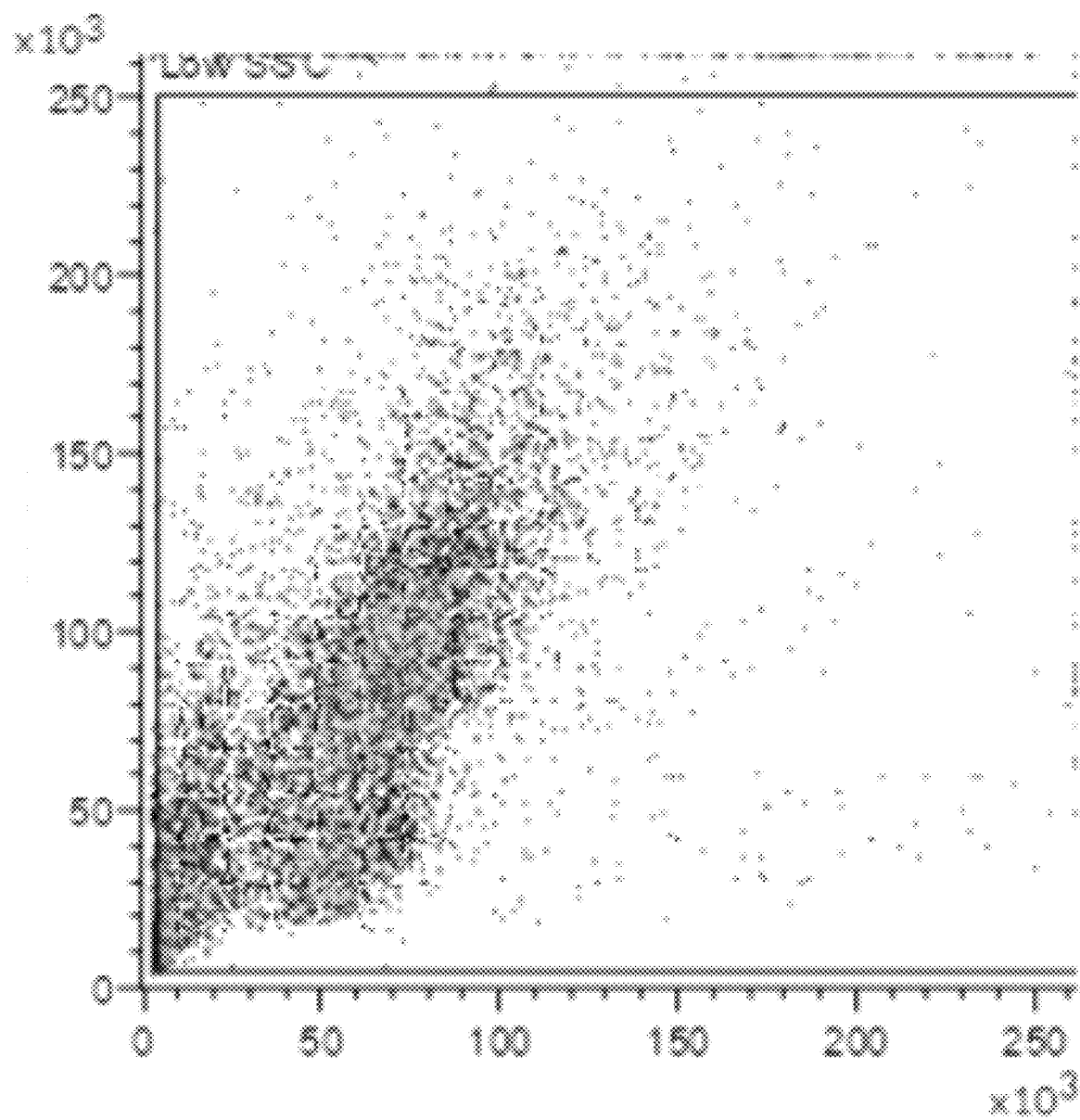

First, all events with very high side scatter (SSC) were excluded, and the remaining cells were then gated for Hoechst$^+$ events. Subsequently, Hoechst$^+$ events were gated for expressing a medium to a high level of CK ($CK^{medium-to-high}$) and being CD45$^-$CD14$^-$. An example of the gating is shown in FIG. 9. Cells were bulk sorted into a 1.5 mL Eppendorf tube containing 25 µL PBS with an event rate of app. 5,000-20,000 events per second. The sorted cells were diluted to a final volume of 500 µL and were then sorted again using the same gating strategy except only gating for cells with a high expression of CK ($CK^{high}$). An example of the gating is shown in FIG. 10. The cells were single cell sorted into PCR tubes containing 5 µL TE buffer with an event rate of app. 100-600 events per second. The event rate was set this low to avoid contamination from maternal cells as the FACS instrument was set to sort in yield mode. The sorted cells were frozen at −80° C. before STR analysis which was performed as described above.

Experimental Results of Example 5

Table 9 depicts the number of sorted cells from the first and the second sort along with the number of fetal cells identified by STR analysis. From the first sort, app. 15,000 to 33,000 cells were sorted, and in the second sort 5-32 cells were sorted. The cells from the second sort were then analysed by STR which revealed between 0 and 9 fetal cells per 10 mL of blood with an average of 2.4 fetal cells. This shows that fetal cell isolation can be done exclusively using FACS and staining of epithelial markers together with CD45, CD14 and Hoechst.

TABLE 9

10 consecutive samples were "double sorted" on a FACS Melody instrument. The first sorting yielded in app. 15,000-32,000 cells and these cells were then loaded again on the FACS and single cell sorted. Between 5 and 32 cells were sorted, and STR analysis showed that 0-9 fetal cells existed among the single cell sorted cells with an average of 2.4.

| Sample ID | Total events (millions) | Sorted cells (1st sort) | Sorted cells (2nd sort) | Fetal cells |
|---|---|---|---|---|
| 3076-WB | 49 | 23,490 | 12 | 9 |
| 3078-WB | 29 | 15,271 | 5 | 0 |
| 3079-WB | 44 | 19,287 | 22 | 1 |
| 3080-WB | 48 | 16,983 | 28 | 0 |
| 3083-WB | 46 | 28,827 | 20 | 3 |
| 3084-WB | 57 | n/a | 20 | 2 |
| 3085-WB | 51 | 32,916 | 30 | 2 |
| 3086-WB | 41 | 22,325 | 17 | 0 |
| 3089-WB | 44 | 16,301 | 32 | 4 |
| 3090-WB | 73 | n/a | 17 | 3 |

Example 6—Enrichment of Fetal Cell Using FACS, Followed by Single Cell Sorting of Fetal Cells Using FACS—Fetal Endothelial Markers In this example, we show that "double-FACS" can identify fetal cells only based on endothelial marker staining (and no epithelial marker staining).

We collected three 10 mL blood samples from pregnant women in gestational week 10-14. Blood processing was performed as described in Example 1.

Fetal Cell Staining

After blood processing, the cells were stained with antibodies targeting one or more of the following antibodies: CD105-FITC, CD141-FITC and CD90-FITC for 15 minutes to 1 h (see antibody combinations in Table 10). Additionally, primary antibodies for CD14 and CD45 and secondary antibodies labelled with AF555 were used for staining the maternal cells. The cells were then washed in PBS, centrifuged at 550 g for 10 minutes, and the supernatant was removed to 500 µL.

FACS Enrichment and Single Cell Sorting

Just before FACS, the cells were stained with 500 µL of a 20 µM Hoechst 33342 solution, and PBS was added to a final volume of 4 mL. The FACS settings were identical to the ones mentioned in example 4, except that the photomultiplier tube voltage for AF488 was set to 461 for the directly conjugated CD105, CD141, and CD90.

Figure 11:
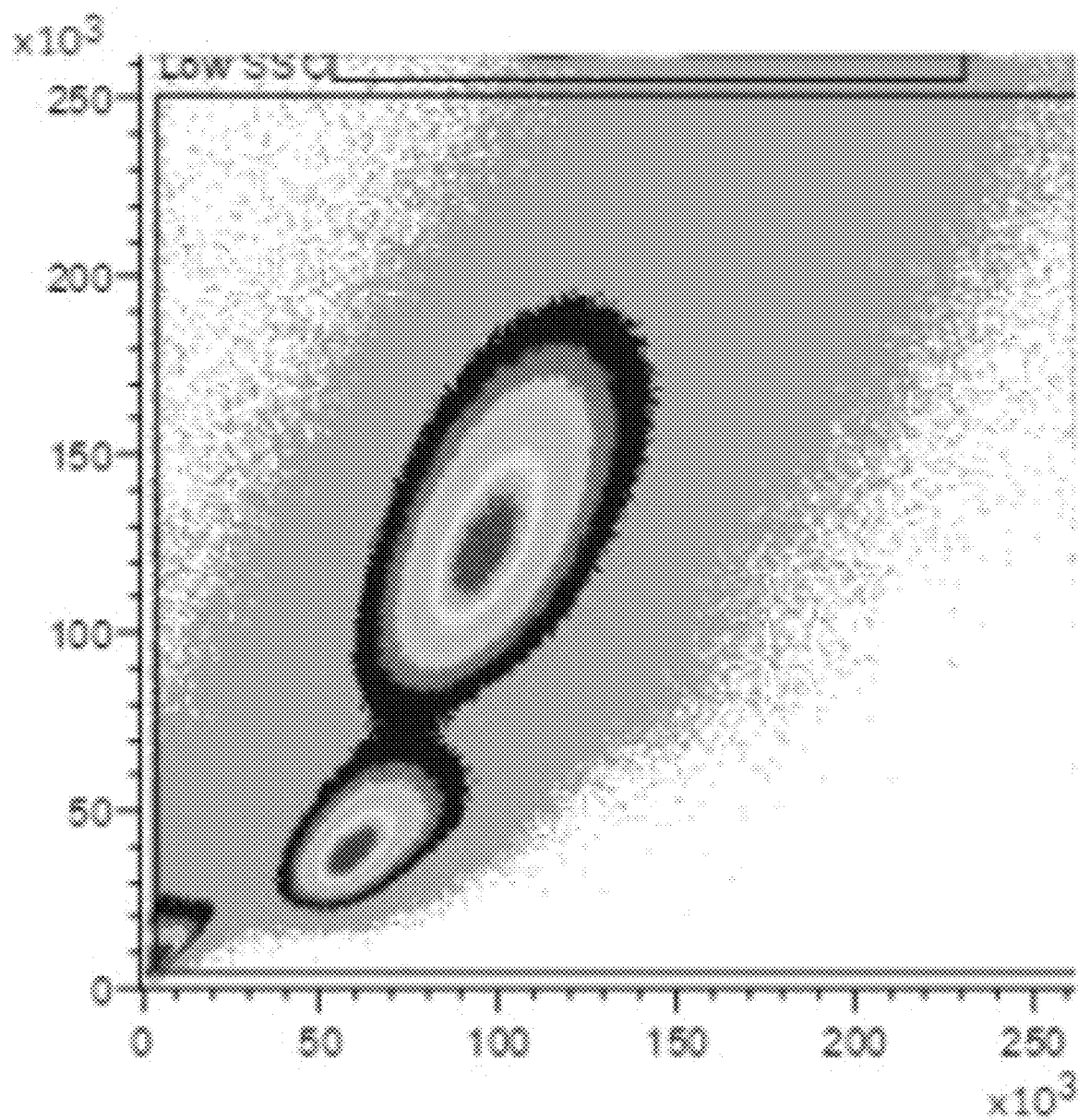
Figure 12:
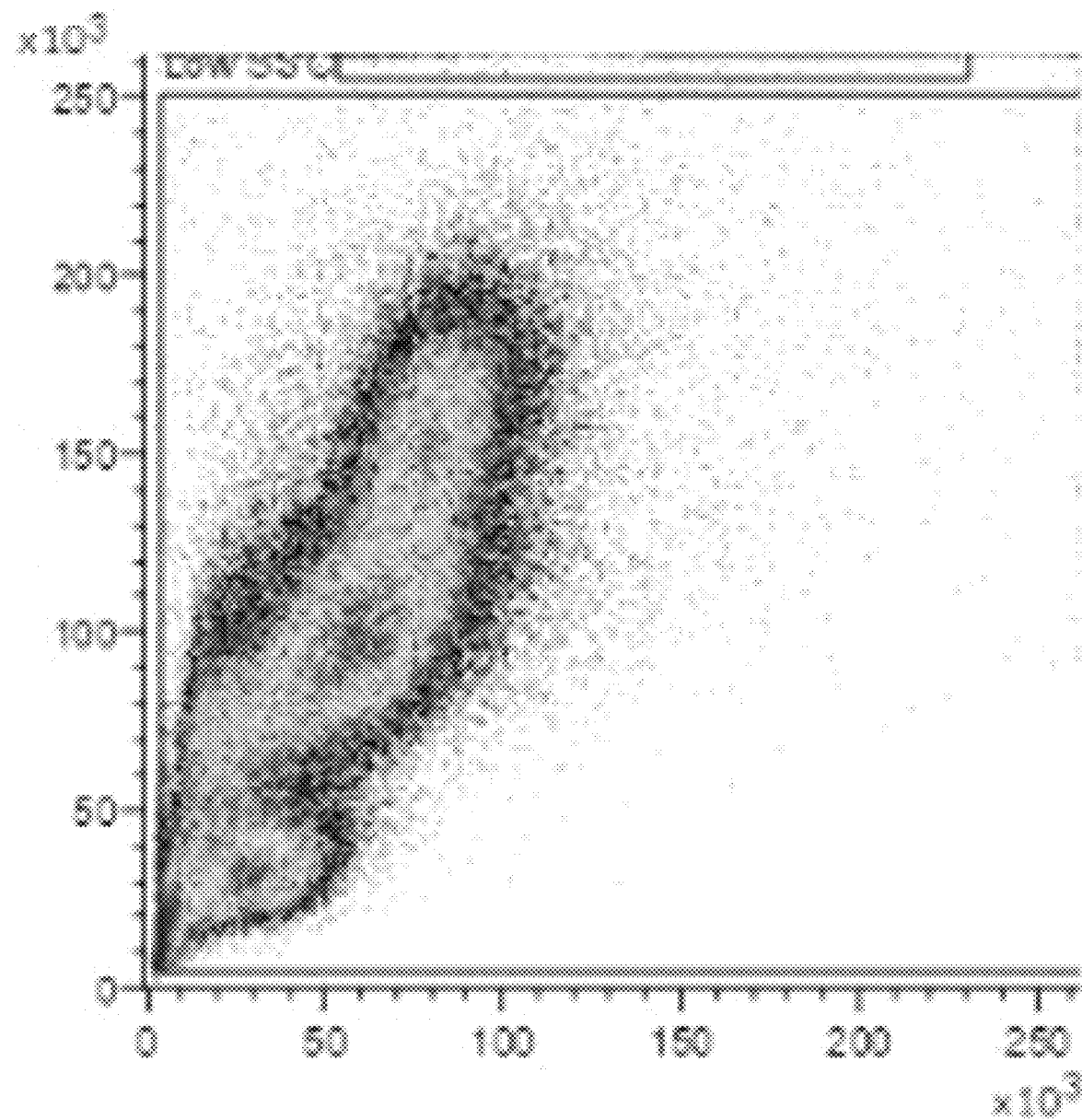

First, all events with very high side scatter (SSC) were excluded, and the low SSC fraction were then gated for Hoechst$^+$ events. Subsequently, Hoechst$^+$ events were gated for expressing a medium to high level of CD105+CD141+CD90. All cells were gated to be CD45$^-$ and CD14$^-$. An example of the gating is shown in FIG. 11. Cells were bulk sorted into a 1.5 mL Eppendorf tube containing 25 µL PBS with an event rate of app. 5,000 to 20,000 events per second. The sorted cells were diluted to a final volume of 500 µL and were then sorted again using the same gating strategy except only cells expressing a high level of CD105+CD141+CD90 were sorted. An example of the gating is shown in FIG. 12. The cells were single cell sorted into PCR tubes 5 µL TE buffer with an event rate of app. 100-600 events per second. The single cell sorted cells were frozen at −80° C. before STR analysis which was performed as described in example 2.

TABLE 10

Endothelial marker staining. Sample HO107-A was stained with antibodies targeting CD105 + CD141 + CD90 and by performing "double FACS", 1 fetal cell was identified. In sample 3091-B, only CD105 and CD141 was stained, and after "double FACS" 1 fetal cell was also detected.

| Sample ID | Sample staining | Total events (millions) | Sorted cells (1st sort) | Sorted cells (2nd sort) | Fetal cells |
|---|---|---|---|---|---|
| H0107-A | CD105 + CD141 + CD90 | 146 | 30,796 | 20 | 1 |
| 3091-B | CD105 + CD141 | 57 | 44,567 | 10 | 1 |

Experimental Results of Example 6

Table 10 shows 2 samples stained with different combinations of endothelial markers. The first sort gave approx. 30,000-45,000 cells whereas the second sort yielded in 10-20 cells. One fetal cell was found in both cases

Example 7—Enrichment of Fetal Cell Using FACS, Followed by Single Cell Sorting of Fetal Cells Using FACS—Different Maternal Cell Specific Markers In the previous examples, staining of CD45 and CD14 have been used for identification of maternal leukocytes while Hoechst has been used for staining of the nuclei. The purposes of these staining were to increase the separation between cells and debris, and between maternal cells and fetal cells. In this example, we investigated if CD45, CD14 and Hoechst were necessary in fetal single cell sorting.

10 mL blood samples were collected from 5 pregnant women in gestational ages of 10-14 weeks. Blood processing was executed as described in example 1. All samples where stained with CK antibodies as described in Example 5. Furthermore, all samples were stained with Hoechst, CD45 and CD14 as described in example 5 unless otherwise stated in Table 11. In one sample, leucocytes were stained with antibodies targeting CD3, CD14, CD15, CD16, and CD19—all directly conjugated to PE for 15 minutes to 1 h. All samples where enriched on FACS using the CK staining together with the leucocyte and Hoechst staining if these were included in the sample as described in Example 5. Finally, the cells were single cell sorted on a FACS instrument using the same staining as for the enrichment FACS. The single cell sorted cells were analysed by STR.

TABLE 11

Maternal marker and Hoechst combinations.

| Sample ID | Sample staining | Total events (millions) | Sorted cells (1st sort) | Sorted cells (2nd sort) | Fetal cells |
|---|---|---|---|---|---|
| AAL302-B | No hoechst, CD45 or CD14 | 33 | 35,000 | 14 | 0 |
| AAL302-A | No CD45 or CD14 | 54 | 13,234 | 15 | 0 |
| KO381 | No CD45 | 23 | 4,806 | 7 | 0 |
| KO380 | No CD14 | 34 | 23,389 | 7 | 3 |

Experimental Results of Example 7

Figure 13:
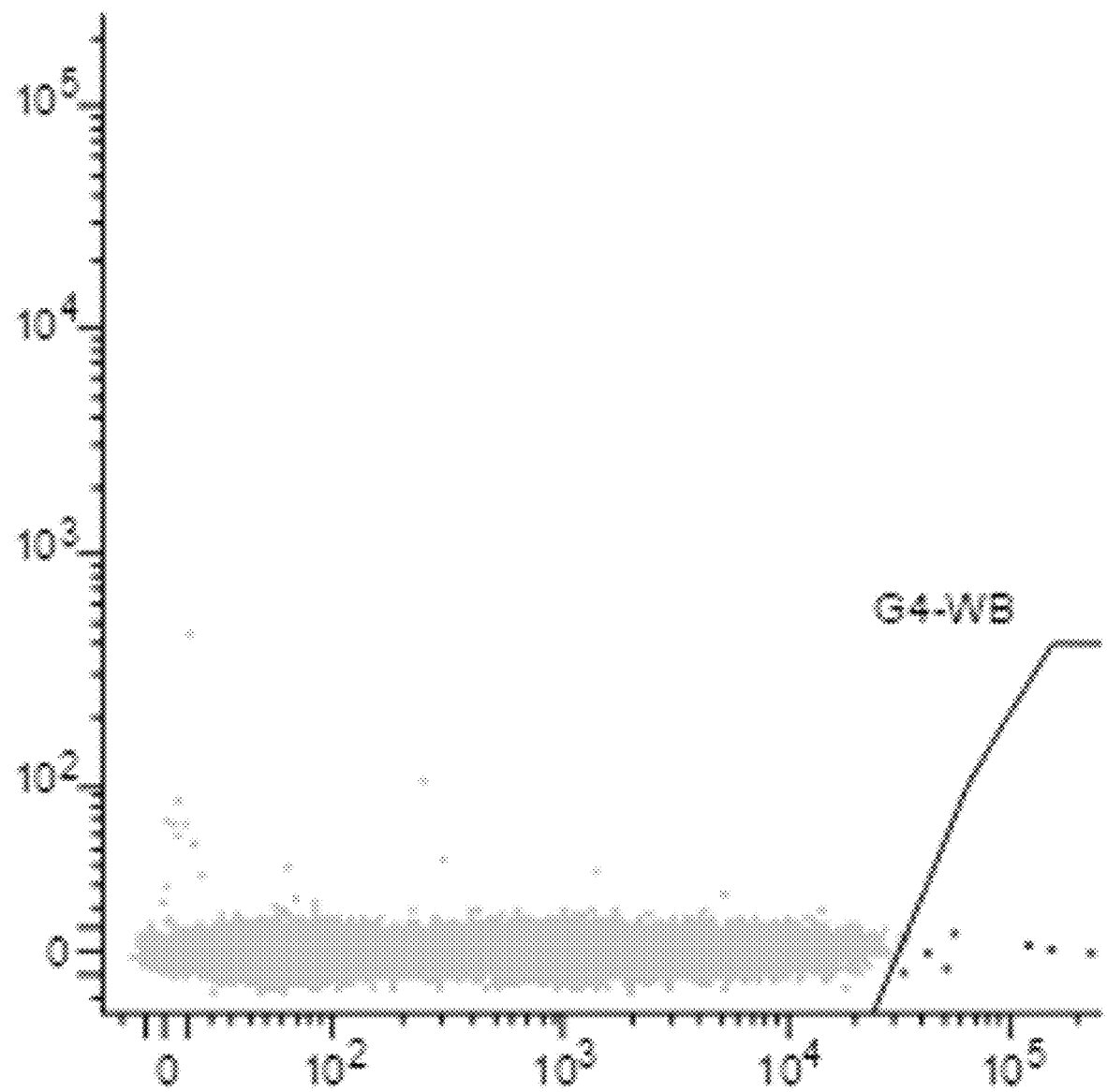

The FACS plot for sample AAL302-B, which was not stained with either Hoechst, CD45 or CD14, can be seen in FIG. 13A. Separation of the cells was greatly decreased. The few events that were separated from the main population were sorted, but STR analysis revealed that all sorted events did not contain DNA, i.e. only debris was sorted. This demonstrates that a nucleus staining such as Hoechst is necessary in order to remove debris from the single cell sorting.

Hoechst:

When Hoechst was added, but no staining of the maternal cells was applied (sample AAL302-A), no clear separation was obtained (FIG. 13B). Only maternal cells were identified by STR, illustrating that staining of maternal markers greatly increases the separation of fetal cells from maternal cells.

Figure 14:
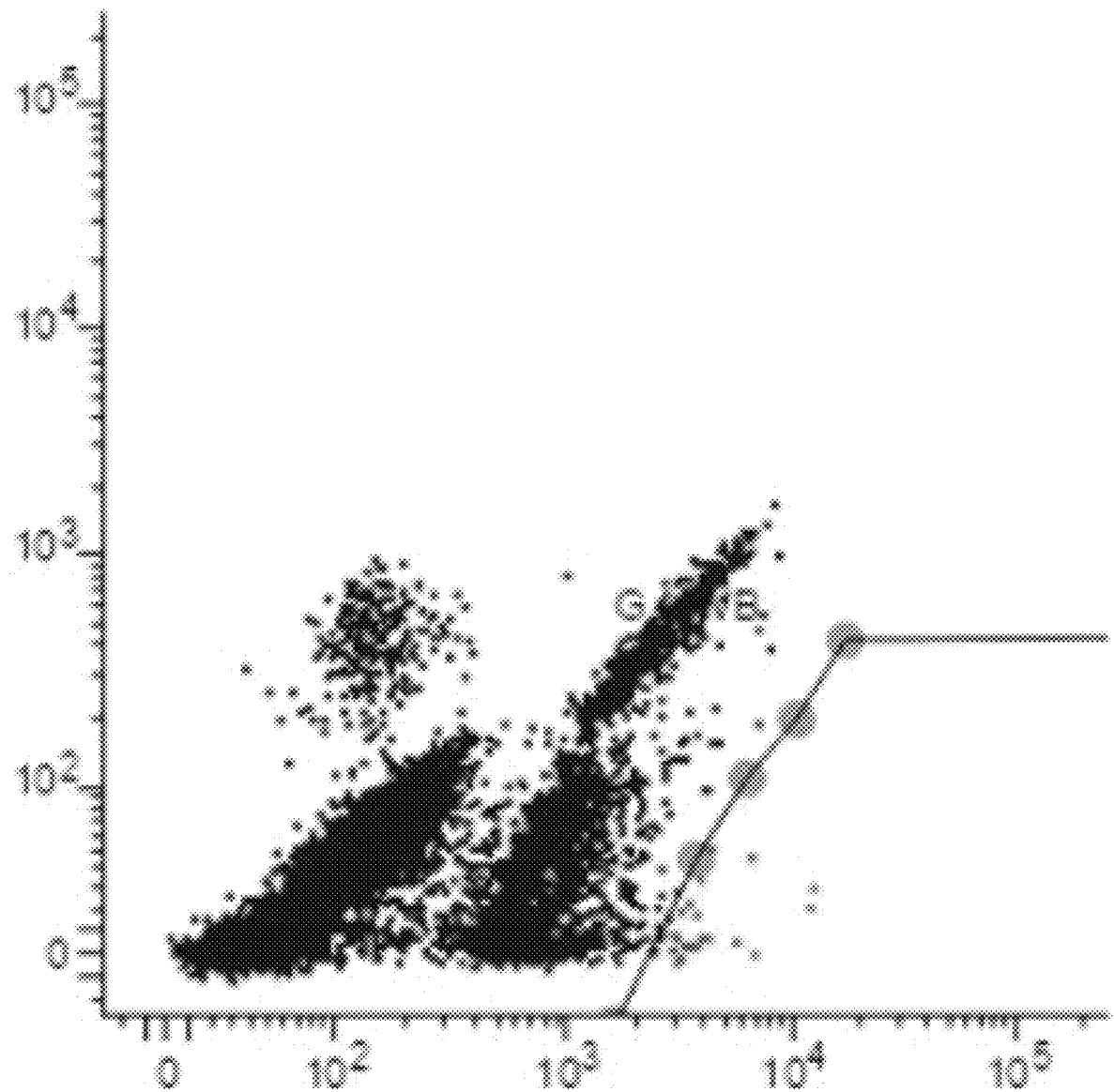

CD14 and CD45:

When the maternal cells were stained with CD14 but not CD45 (sample K0381), a separation was obtained, but no fetal cells were identified (FIG. 14A). However, when only CD45 staining was performed and not CD14 staining (sample K0380, FIG. 14B), 3 fetal cells were identified, showing that CD45 staining is essential.

Other Leucocyte Markers:

CD45 is also known as the common leucocyte antigen as it is expressed on all subgroups of leucocytes (monocytes, granulocytes, T cells, B cells, and NK cells). Therefore, to investigate if CD45 could be replaced by markers representing all subgroups of leucocytes, we stained CD3 (T cells), CD14 (monocytes), CD15 (granulocytes), CD16 (NK cells), and CD19 (B cells) together with CKs and Hoechst staining as previously described in Example 5. This resulted in 3 fetal cells (Table 12), demonstrating that CD45 can be replaced by a group of other leucocyte markers.

TABLE 12

CD3, CD14, CD15, CD16, and CD19 target the different subgroups of leucocytes in peripheral blood. By staining the different subgroups instead of CD45 which targets all subgroups, 3 fetal cells were identified.

| Sample ID | Sample staining | Total events (millions) | Sorted cells (1st sort) | Sorted cells (2nd sort) | Fetal cells |
|---|---|---|---|---|---|
| 3091-A | CD3, CD14, CD15, CD16, and CD19 | 57 | 11,058 | 25 | 3 |

Items

1. A method of isolating fetal cells comprising the steps of:
   1. providing a biological sample from a woman carrying a fetus,
   2. enriching said sample for fetal cells,
   3. contacting said sample with at least one fluorescent labelling agent,
   4. single cell sorting at least one fetal cell on a fluorescence activated cell sorter (FACS) from said enriched sample.

2. A method of prenatal diagnostics comprising the steps of:
   1. obtaining at least one fetal cell isolated by a method as defined in item 1
   2. obtaining a genotype from said fetal cell, and
   3. diagnosing the phenotype of the fetus.

3. A method of prenatal diagnostics comprising the steps of:
   1. providing a biological sample from a woman carrying a fetus,
   2. enriching said sample for fetal cells,
   3. contacting said sample with at least one fluorescent labelling agent
   4. single cell sorting at least one fetal cell on a fluorescence activated cell sorter (FACS) from said enriched sample
   5. obtaining a genotype from said fetal cell, and
   6. diagnosing the phenotype of the fetus.

4. The method according to any of the preceding items, wherein said fluorescent labelling agent is directed against the nucleus, a fetal cell marker and/or a maternal cell marker.

5. The method according to any of the preceding items, wherein said at least one fluorescent labelling agent is selected from each of the groups:
   i. fluorescent labelling agent directed against the nucleus,
   ii. fluorescent labelling agent directed against a maternal cell marker, and
   iii. fluorescent labelling agent directed against a fetal cell marker 6. The method according to any of the preceding items, wherein the sample is enriched with magnetic activated cell sorting (MACS).

7. The method according to item 6, wherein the enrichment step is preceded by a step of contacting cells comprised in said sample sample with at least one magnetically labelled agent directed against a fetal cell marker.

8. The method according to any of items 1-5, wherein the sample is enriched on a fluorescence activated cell sorter (FACS).

9. The method according to item 8, wherein the enrichment step is preceded by a step of contacting cells comprised in said biological sample with at least one fluorescent labelling agent selected from each of the groups:
   i. fluorescent labelling agent directed against the nucleus,
   ii. fluorescent labelling agent directed against a maternal cell marker, and
   iii. fluorescent labelling agent directed against a fetal cell marker 10. The method according to item 9, wherein said enrichment on a fluorescence activated cell sorter (FACS) is based on fluorescence from said fluorescent labelling agents.

11. The method according to any of the preceding items, wherein said at least one single cell sorted fetal cell is sorted on a fluorescence activated cell sorter (FACS) based on:
    i. positive selection of said fluorescent labelling agent directed against a fetal cell marker,
    ii. positive selection of said fluorescent labelling agent directed against the nucleus, and
    iii. negative selection of said fluorescent labelling agent directed against a maternal cell marker 12. The method according to any of the preceding items, wherein said fetal cells are fetal trophoblasts, such as extravillous trophoblasts, endovascular trophoblasts, cytotrophoblasts and/or syncytiotrophoblast.

13. The method according to any of the preceding items, wherein said magnetic- and/or fluorescent labelling agent directed against a fetal trophoblast marker is a magnetic- and/or fluorescent labelling agent directed against an endothelial or an epithelial marker.

14. The method according to any of the preceding items, wherein said magnetic- and/or fluorescent labelling agent directed against a fetal trophoblast marker is a magnetic- and/or fluorescent labelling agent directed against an endothelial marker.

15. The method according to any of the preceding items, wherein said endothelial marker is selected from Thy-1 CD90, Thrombomodulin CD141, Human Endoglin CD105, Human Vimentin (Vim), Vascular Cell Adhesion Molecule (VCAM), Intercellular Adhesion Molecule 1 (ICAM), Vascular Endothelial Growth Factor Receptor 1 (Flt-1)

(VEGFR-1), Vascular Endothelial Growth Factor Receptor 2 (VEGFR-2), Vascular Endothelial Growth Factor Receptor 3 (VEGFR-3), Plasminogen Activator Inhibitor 1 (PAI-1), Endothelial Protein C Receptor (EPCR), CD146, ITGA5, ITGB5, CDH11, CDH3 and/or CD59.

16. The method according to any of the preceding items, wherein said endothelial markers is CD105, CD90 and/or CD141.

17. The method according to any of the preceding items, wherein said endothelial markers is CD105 and/or CD141.

18. The method according to any of the preceding items, wherein said magnetic- and/or fluorescent labelling agent directed against a fetal trophoblast marker is a magnetic- and/or fluorescent labelling agent directed against an epithelial marker.

19. The method according to any of the preceding items, wherein said epithelial marker is a cytokeratin.

20. The method according to any of the preceding items, wherein said epithelial marker is a cytokeratin such as Human Cytokeratin 1 CK1, Human Cytokeratin 2 CK2, Human Cytokeratin 3 CK3, Human Cytokeratin 4 CK4, Human Cytokeratin 5 CK5, Human Cytokeratin 6 CK6, Human Cytokeratin 7 CK7, Human Cytokeratin 8 CK8, Human Cytokeratin 9 CK9, Human Cytokeratin 10 CK10, Human Cytokeratin 13 CK13, Human Cytokeratin 14 CK14, Human Cytokeratin 15 CK15, Human Cytokeratin 16 CK16, Human Cytokeratin 17 CK17, Human Cytokeratin 18 CK18, Human Cytokeratin 19 CK19.

21. The method according to any of the preceding items, wherein said epithelial marker is a cytokeratin, Human Cytokeratin 7 CK7, Human Cytokeratin 8 CK8, Human Cytokeratin 18 CK18 and/or Human Cytokeratin 19 CK19.

22. The method according to any of the preceding items, wherein said epithelial marker is Human Cytokeratin 7 CK7, Human Cytokeratin 8 CK8, Human Cytokeratin 18 CK18 and/or Human Cytokeratin 19 CK19.

23. The method according to any of the preceding items, wherein said fluorescent labelling agents are antibodies, nucleotide probes, receptor ligands, and/or other specific binding molecules.

24. The method according to any of the preceding items, wherein said at least one fluorescent labelling agents are directly or indirectly labelled by at least one fluorophore.

25. The method according to item 40, wherein said fluorophore is selected from the group consisting of Alexa Fluor 488, Alexa Fluor 555, Fluorescein isothiocyanate (FITC), Phycoerythrin (PE), and BV421.

26. The method according to any of the preceding items, wherein said fluorescent labelling agent directed against the nucleus is selected from any Hoechst dye, DAPI, propidium iodide, 7-AAD, Vybrant DyeCycle Stains, SYTOX stains, or SYTO stains.

27. The method according to any of the preceding items, wherein said fluorescent labelling agent directed against the nucleus is Hoechst 33342.

28. The method according to any of the preceding items, wherein said fluorescent labelling agent directed against a maternal cell marker is a fluorescent labelling agent directed against a leucocyte.

29. The method according to any of the preceding items, wherein said leucocyte marker is selected from CD45, CD3, CD14, CD15, CD16, and/or CD19.

30. The method according to any of the preceding items, wherein said leucocyte marker is CD45 and CD14.

31. The method according to any of the preceding items, wherein said leucocyte marker is CD45.

32. The method according to any of the preceding items, wherein said genotype is obtained by STR analysis.

33. The method according to any of the preceding items, wherein said genotype is obtained by SNP analysis.

34. The method according to any of the preceding items, wherein said phenotype is diagnosed by detecting one or more markers associated with a genetic abnormality in the genome of the fetal cell.

35. The method according to any of the preceding items, wherein said genetic abnormality is detected by one or more method selected from Microarray-based Comparative Genomic Hybridization (aCGH), Short Tanden Repeat analysis (STR analysis), whole genome amplification, whole genome scan, SNP array, Polony sequencing, Shotgun sequencing, Massively parallel signature sequencing (MPSS), Sanger Sequencing, PCR-based methods and Next-Generation Sequencing methods.

36. The method according to any of the preceding items, wherein said Next-Generation Sequencing methods can be selected from the group consisting of Illumina (Solexa) sequencing, Roche 454 sequencing, Ion torrent: Proton/PGM sequencing and/or SOLiD sequencing.

37. The method according to any of the preceding items, wherein said genetic abnormality is aneuploidy, monosomy, polysomy, trisomy, copy number variation (CNV), single nucleotide variation (SNV), or a monogenic disorder.

38. The method according to any of the preceding items, wherein said biological sample comprises a cellular fraction.

39. The method according to any of the preceding items, wherein said cellular fraction comprises both maternal cells and fetal cells.

40. The method according to any of the preceding items, wherein said biological sample is a blood sample.

41. The method according to any of the preceding items, wherein said blood sample is between 5-30 mL.

42. The method according to any of the preceding items, wherein said blood sample is a 30 mL blood sample.

43. The method according to any of the preceding items, wherein said blood sample is a 10 mL blood sample.

44. A method of prenatal diagnostics comprising the steps of:
   1. providing a blood sample from a woman carrying a fetus,
   2. contacting cells comprised in said blood sample with at least one labelling agent directed against a fetal trophoblast marker,
   3. enriching said sample for fetal trophoblasts with a microfluidic device,
   4. contacting said sample with at least one fluorescent labelling agent selected from each of the groups:
      i. fluorescent labelling agent directed against the nucleus,
      ii. fluorescent labelling agent directed against a maternal cell marker, and
      iii. fluorescent labelling agent directed against a fetal trophoblast marker
   5. single cell sorting at least one fetal trophoblast on a fluorescence activated cell sorter (FACS) from said enriched sample based on:
      i. positive selection of said fluorescent labelling agent directed against a fetal trophoblast marker,
      ii. positive selection of said fluorescent labelling agent directed against the nucleus, and
      iii. negative selection of said fluorescent labelling agent directed against a maternal cell marker
   6. obtaining a genotype from said fetal trophoblast, and
   7. diagnosing the phenotype of the fetus.

Elements

1. A method of isolating fetal cells from a biological sample of a pregnant woman, said method comprising the steps of
   a. providing a biological sample from said pregnant woman, the biological sample comprising a cellular fraction,
   b. contacting cells comprised in said cellular fraction with one or more fluorescent labelling agents directed against at least one fetal cell epithelial marker and/or endothelial marker,
   c. sorting said cells by Fluorescence-activated cell sorting (FACS) based on detection of said one or more fluorescent labelling agents bound to cells, and
   d. identifying fetal cells among said sorted cells comprising a step of assigning a fetal origin classifier to individual sorted cells.

2. The method according to any of the preceding elements, wherein the cellular fraction is enriched for fetal cells prior to FACS.

3. The method according to element 2, wherein the enrichment comprises enriching for cells expressing at least one endothelial marker.

4. The method according to elements 2 or 3, wherein enrichment comprises magnetic activated cell sorting.

5. The method according to any of the preceding elements, wherein the FACS comprises quantifying a number of parameters for each sorted cell.

6. The method according to element 5, wherein the parameters are scatter, such as forward and side scatter; fluorescence from a nuclear dye; fluorescence from a fluorescent labelling agent bound to at least one fetal marker; and fluorescence from a fluorescent labelling agent bound to at least one maternal marker.

7. The method of element 6, wherein the fetal marker is one or more epithelial markers, such as one or more cytokeratins, and/or wherein the maternal marker is a blood cell marker, such as CD14 and/or CD45.

8. The method according to any of the preceding elements, wherein a further parameter is fluorescence from one or more fluorescent labelling agent directed to endothelial markers, such as CD105 and/or CD141.

9. The method according to any of the preceding elements, wherein the fetal origin classifier is a binary classifier classifying the cell as fetal or non-fetal.

10. The method according to any of the preceding elements, wherein the fetal origin classifier is a probability of fetal origin.

11. The method according to any of the preceding elements, wherein said fetal origin classifier is calculated using artificial intelligence, neural network, random forest, machine learning, regression analysis, or classification trees using a training set comprising fetal and maternal cells.

12. The method of element 11, wherein the regression analysis is logistic regression.

13. The method according to element 12, wherein said logistic regression comprises a constant parameter and specific values for the detected parameters to calculate a probability.

14. The method according to any preceding elements, wherein said sorted cells are cells that express at least one epithelial marker and/or endothelial marker and do not express at least one cell marker specific for blood cells.

15. The method of element 14, wherein cells positive for the at least one epithelial marker and being negative or low for said at least one blood cell marker are sorted into compartments, preferably wherein each compartment comprises only one cell.

16. The method according to any preceding elements, wherein said biological sample is a peripheral blood sample or a cervical smear.

17. The method according to any preceding elements, wherein a cellular fraction is separated from plasma of said peripheral blood sample.

18. The method according to any of the preceding elements, wherein said cellular fraction is separated from said plasma fraction by centrifugation.

19. The method according to any preceding elements, wherein said cellular fraction comprises red blood cells, white blood cells and fetal trophoblasts, fetal extravillous trophoblasts, and fetal endovascular trophoblasts.

20. The method according to any of the preceding elements, said method further comprising a step of fixating the blood cells subsequent to being separated from said plasma fraction, wherein fixation is preferably a paraformaldehyde fixation.

21. The method according to any of the preceding elements, said method further comprising a step of selectively lysing red blood cells of said cellular fraction using a detergent subsequent to separation of said cellular fraction from said plasma fraction, wherein said lysing also permeabilizes the remaining cells in said cellular fraction.

22. The method according to element 1, wherein the biological sample is a cervical smear.

23. The method according to element 22, wherein said cervical smear is subjected to acetic acid or DDT to dissolve mucus, followed by fixation, wherein fixation is preferably a paraformaldehyde fixation.

24. The method according to elements 22 and 23, wherein said cellular fraction from the cervical smear comprises fetal cells and squamous epithelial cells, columnar epithelial cells, white blood cells and red blood cells.

25. The method according to any preceding elements, wherein said fetal cells are trophoblasts, such as cytotrophoblasts and/or syncytiotrophoblasts.

26. The method according to any preceding elements, wherein said isolated fetal cells are verified as fetal cells by having a fetal genotype distinct from the maternal genotype.

27. The method according to any of the preceding elements, wherein isolated fetal cells are subjected to whole genome amplification.

28. The method according to element 26 or 27, wherein said verification is performed by detection of short tandem repeats or single nucleotide polymorphisms (SNPs).

29. The method according to element 26 or 27, wherein the 20 cells with the highest probability of fetal origin are subjected to whole genome verification and/or are verified as fetal cells, such at the 15 cells with the highest probability, for example the 10 cells with the highest probability, such as the 7 cells with the highest probability, for example the 5 cells with the highest probability, such as the 3 cells with the highest probability.

30. The method according to any of the preceding elements, wherein the method results in identification of at least 1 fetal cells in one biological sample from one pregnant mother, wherein the biological sample comprises at least 150 mio cells, such as at least 2 fetal cells, for example at least 3 fetal cells.

31. The method according to any preceding elements, wherein said at least one epithelial marker is selected from the group consisting of Human Cytokeratin 1 CK1, Human Cytokeratin 2 CK2, Human Cytokeratin 3 CK3, Human Cytokeratin 4 CK4, Human Cytokeratin 5 CK5, Human Cytokeratin 6 CK6, Human Cytokeratin 7 CK7, Human Cytokeratin 8 CK8, Human Cytokeratin 10 CK10, Human Cytokeratin 13 CK13, Human Cytokeratin 14 CK14, Human Cytokeratin 15 CK15, Human Cytokeratin 16 CK16, Human Cytokeratin 17 CK17, Human Cytokeratin 18 CK18, Human Cytokeratin 19 CK19.

32. The method according to any preceding elements, wherein said at least one epithelial marker is CK7, CK18 or a combination thereof.

33. The method of any of elements 31 and 32, wherein antibodies against epithelial markers are linked to the same fluorophore.

34. The method according to any preceding elements, wherein said at least one endothelial marker is selected from the group consisting of Thrombomodulin CD141, Human Endoglin CD105, Human Vimentin Vim, Vascular Cell Adhesion Molecule VCAM, Intercellular Adhesion Molecule 1 ICAM, Vascular Endothelial Growth Factor Receptor 1 (Flt-1) VEGFR-1, Vascular Endothelial Growth Factor Receptor 2 VEGFR-2, Vascular Endothelial Growth Factor Receptor 3 VEGFR-3, Plasminogen Activator Inhibitor 1 PAI-1, Endothelial Protein C Receptor EPCR.

35. The method according to any preceding elements, wherein said at least one endothelial marker is CD105, CD141 or a combination thereof.

36. The method of any of the elements 34 and 35, wherein antibodies against endothelial markers are labelled with the same fluorophore.

37. The method according to any preceding elements, wherein said at least one cell marker specific for blood cells is CD14 and/or CD45, preferably wherein antibodies against different blood cell markers are labelled with the same fluorophore.

38. The method according to any preceding elements, wherein said identified fetal cells express said at least one epithelial marker and/or endothelial marker and do not express said at least one cell marker specific for blood cells.

39. The method according to any preceding elements, wherein said at least one fluorescent nuclear dye is an intercalating DNA dye, for example any Hoechst dye, DAPI, propidium iodide, 7-AAD, Vybrant DyeCycle Ruby Stain.

40. The method according to any preceding elements, wherein said one or more fluorescent labelling agents are directly or indirectly labelled by at least one fluorophore.

41. The method according to element 40, wherein said fluorophore is selected from the group consisting of Alexa Fluor 488, Alexa Fluor 555, Fluorescein isothiocyanate (FITC), Phycoerythrin (PE), and BV421.

42. The method according to element 40, wherein said fluorescent labelling agents are indirectly labelled by a secondary labelling agent.

43. The method according to any of the preceding elements, wherein the fluorescent labelling agents are antibodies, nucleotide probes, receptor ligands, or other specific binding molecules.

44. The method of element 43, wherein the nucleotide probe is an RNA, a DNA, or an LNA probe.

45. The method according to any preceding elements, wherein said method further comprises a step of detecting one or more genetic markers associated with a genetic abnormality in the genome of said isolated fetal cells.

46. The method according to element 45, wherein said one or more genetic markers is associated with aneuploidy, monosomy, polysomy, trisomy, copy number variation (CNV), single nucleotide variation (SNV), or a monogenic disorder.

47. A method of determining a genetic abnormality in a fetus said method comprising the steps of a. Obtaining one or more fetal cells isolated by a method as defined in any of the preceding elements 1 to 46, and
b. Detecting one or more genetic markers associated with said genetic abnormality in the genome of said fetal cell 48. The method according to element 47, wherein said one or more genetic markers are detected using one or more methods selected from the group consisting of Microarray-based Comparative Genomic Hybridization (aCGH), Short Tandem Repeat analysis (STR analysis), whole genome amplification, whole genome scan, Polony sequencing, Shotgun sequencing, Massively parallel signature sequencing (MPSS), Sanger Sequencing, PCR-based methods and Next-Generation Sequencing methods.

49. The method according to element 48, wherein said Next-Generation Sequencing methods can be selected from the group consisting of Illumina (Solexa) sequencing, Roche 454 sequencing, Ion torrent: Proton/PGM sequencing and/or SOLiD sequencing.

50. The method according to element 47, wherein said genetic abnormality is aneuploidy, monosomy, polysomy, trisomy, copy number variation (CNV), single nucleotide variation (SNV), or a monogenic disorder.

The invention claimed is:

1. A method of prenatal diagnostics comprising the steps of:
  A. providing a blood sample from a woman carrying a fetus;
  B. contacting cells comprised in said blood sample with at least one magnetic labelling agent directed against a fetal trophoblast marker;
  C. enriching said sample for fetal trophoblasts with magnetic activated cell sorting (MACS) to form enriched cells;
  D. contacting the enriched cells with at least one fluorescent labelling agent selected from each of the groups to form fluorescently labelled cells:
    i. fluorescent labelling agent directed against the nucleus,
    ii. fluorescent labelling agent directed against a maternal cell marker, and
    iii. fluorescent labelling agent directed against a fetal trophoblast marker;
  E. single cell sorting the fluorescently labelled cells on a fluorescence activated cell sorter (FACS), wherein single cell sorted cells are sorted into single cell compartments based on detection by said FACS and based on:
    iv. positive selection of said fluorescent labelling agent directed against a fetal trophoblast marker,
    v. positive selection of said fluorescent labelling agent directed against the nucleus, and
    vi. negative selection of said fluorescent labelling agent directed against a maternal cell marker;
  F. identifying fetal trophoblasts among said single cell sorted cells, comprising a step of assigning a fetal origin classifier to individually sorted cells by obtaining a genotype from the single sorted cells; and
  G. diagnosing the phenotype of the fetus.

2. The method according to claim 1, wherein said magnetic-labelling agent directed against a fetal trophoblast marker is a magnetic-labelling agent directed against an endothelial marker.

3. The method according to claim 2, wherein said endothelial markers is CD105, CD90 and/or CD141.

4. The method according to claim 1, wherein said fluorescent labelling agent directed against a fetal trophoblast marker is a fluorescent labelling agent directed against an epithelial marker.

5. The method according to claim 4, wherein said epithelial marker is a cytokeratin, Human Cytokeratin 7 (CK7), Human Cytokeratin 8 (CK8), Human Cytokeratin 18 (CK18) and/or Human Cytokeratin 19 (CK19).

6. The method according to claim 1, wherein said magnetic and/or fluorescent labelling agents are antibodies.

7. The method according to claim 1, wherein said at least one of said fluorescent labelling agents are indirectly and/or directly labelled by at least one fluorophore.

8. The method according to claim 7, wherein said fluorophore is selected from the group consisting of Alexa Fluor 488, Alexa Fluor 555, Fluorescein isothiocyanate (FITC), Phycoerythrin (PE), and BV421.

9. The method according to claim 1, wherein said fluorescent labelling agent directed against the nucleus is selected from any Hoechst dye, such as Hoechst 33342, DAPI, propidium iodide, 7-AAD, Vybrant DyeCycle Stains, SYTOX stains, or SYTO stains.

10. The method according to claim 1, wherein said fluorescent labelling agent directed against a maternal cell marker is a fluorescent labelling agent directed against a leucocyte marker selected from CD45, CD3, CD14, CD15, CD16, and/or CD19.

11. The method according to claim 1, wherein said genotype is obtained by STR analysis or SNP analysis.

12. The method according to claim 1, wherein said phenotype is diagnosed by detecting one or more markers associated with a genetic abnormality in the genome of the fetal cell.

13. The method according to claim 12, wherein said genetic abnormality is detected by one or more methods selected from Microarray-based Comparative Genomic Hybridization (aCGH), Short Tanden Repeat analysis (STR analysis), whole genome amplification, whole genome scan, SNP array, Polony sequencing, Shotgun sequencing, Massively parallel signature sequencing (MPSS), Sanger Sequencing, PCR-based methods and Next-Generation Sequencing methods.

14. The method according to claim 12, wherein said genetic abnormality is aneuploidy, monosomy, polysomy, trisomy, copy number variation (CNV), single nucleotide variation (SNV), or a monogenic disorder.

15. The method according to claim 1, wherein said blood sample is between 5-50 mL.

16. The method according to claim 1, wherein said blood sample comprises a cellular fraction separated from plasma of said blood sample.

17. The method according to claim 16, wherein said cellular fraction comprises both maternal cells and fetal cells.

18. The method according to claim 16, said method further comprising a step of fixating the cells in said blood sample subsequent to being separated from plasma, wherein fixation is optionally a paraformaldehyde fixation.

19. The method according to claim 16, said method further comprising a step of selectively lysing red blood cells of said cellular fraction using a detergent subsequent to separation of said cellular fraction from said plasma fraction, wherein said lysing also permeabilizes the remaining cells in said cellular fraction.

* * * * *